United States Patent
Okazaki et al.

(10) Patent No.: US 9,765,672 B2
(45) Date of Patent: Sep. 19, 2017

(54) CONTROL SYSTEM OF INTERNAL COMBUSTION ENGINE

(71) Applicants: Shuntaro Okazaki, Shizuoka (JP); Norihisa Nakagawa, Susono (JP); Yuji Yamaguchi, Susono (JP)

(72) Inventors: Shuntaro Okazaki, Shizuoka (JP); Norihisa Nakagawa, Susono (JP); Yuji Yamaguchi, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 14/763,370

(22) PCT Filed: Jan. 29, 2013

(86) PCT No.: PCT/JP2013/051911
§ 371 (c)(1),
(2) Date: Jul. 24, 2015

(87) PCT Pub. No.: WO2014/118892
PCT Pub. Date: Aug. 7, 2014

(65) Prior Publication Data
US 2016/0061084 A1 Mar. 3, 2016

(51) Int. Cl.
*F01N 3/20* (2006.01)
*F01N 9/00* (2006.01)
(Continued)

(52) U.S. Cl.
CPC .............. *F01N 9/00* (2013.01); *F01N 11/007* (2013.01); *F02D 41/0295* (2013.01);
(Continued)

(58) Field of Classification Search
CPC ......... F02D 41/0295; F02D 2200/0814; F02D 2200/0816; F01N 2900/1624
See application file for complete search history.

(56) References Cited

U.S. PATENT DOCUMENTS

| 5,758,490 A | 6/1998 | Maki et al. |
| 6,055,972 A | 5/2000 | Fujimoto et al. |

(Continued)

FOREIGN PATENT DOCUMENTS

| JP | H04-204370 A | 7/1992 |
| JP | H08-232723 A | 9/1996 |

(Continued)

*Primary Examiner* — Jonathan Matthias
(74) *Attorney, Agent, or Firm* — Andrews Kurth Kenyon LLP

(57) ABSTRACT

This control device for an internal combustion engine equipped with an exhaust purification catalyst, which is disposed in an exhaust passage of the internal combustion engine and capable of storing oxygen, includes: a downstream air-fuel ratio detection means that is disposed downstream of the exhaust purification catalyst in the exhaust flow direction; and an inflow air-fuel ratio control means that controls the air-fuel ratio of exhaust gas flowing into the exhaust purification catalyst. If the outflow air-fuel ratio detected by the downstream air-fuel ratio detection means is equal to or less than a rich-determination air-fuel ratio, which is richer than the stoichiometric air-fuel ratio, the inflow air-fuel ratio control means sets the target air-fuel ratio of exhaust gas flowing into the exhaust purification catalyst continuously or intermittently leaner than the stoichiometric air-fuel ratio until the oxygen storage amount of the exhaust purification catalyst reaches a prescribed storage amount. If the oxygen storage amount of the exhaust purification catalyst is equal to or greater than the prescribed storage amount, the inflow air-fuel ratio control means sets the target air-fuel ratio continuously or intermittently richer than the stoichiometric air-fuel ratio until the oxygen storage amount decreases toward zero without reaching the maximum oxygen storage amount.

18 Claims, 17 Drawing Sheets

(51) Int. Cl.
  *G01N 27/41* (2006.01)
  *F02D 41/02* (2006.01)
  *F02D 41/14* (2006.01)
  *F01N 11/00* (2006.01)
  *F01N 13/00* (2010.01)

(52) U.S. Cl.
  CPC ..... *F02D 41/1454* (2013.01); *F02D 41/1475* (2013.01); *G01N 27/41* (2013.01); *F01N 13/009* (2014.06); *F01N 13/0093* (2014.06); *F01N 2430/06* (2013.01); *F01N 2560/025* (2013.01); *F01N 2560/14* (2013.01); *F01N 2900/1624* (2013.01)

(56) References Cited

U.S. PATENT DOCUMENTS

| | | |
|---|---|---|
| 2003/0017603 A1 | 1/2003 | Uchida et al. |
| 2007/0095051 A1 | 5/2007 | Iihoshi et al. |
| 2010/0242934 A1 | 9/2010 | Yonekawa et al. |
| 2012/0060805 A1 | 3/2012 | Nakano et al. |
| 2013/0269324 A1 | 10/2013 | Onoe et al. |

FOREIGN PATENT DOCUMENTS

| | | |
|---|---|---|
| JP | H10-82760 A | 3/1998 |
| JP | 2001-098982 A | 4/2001 |
| JP | 2001-234787 A | 8/2001 |
| JP | 2002-364428 A | 12/2002 |
| JP | 2005-002867 A | 1/2005 |
| JP | 2005-127259 A | 5/2005 |
| JP | 2006-104970 A | 4/2006 |
| JP | 2007-126982 A | 5/2007 |
| JP | 2009-162139 A | 7/2009 |
| JP | 2010-236450 A | 10/2010 |
| JP | 2011-069337 A | 4/2011 |
| JP | 2011-127567 A | 6/2011 |
| WO | 2010/134209 A1 | 11/2010 |
| WO | 2012/035622 A1 | 3/2012 |

(A)

(B)

(A)

(B)

(C)

(A)

(B)

(C)

CONTROL SYSTEM OF INTERNAL COMBUSTION ENGINE

CROSS-REFERENCE TO RELATED APPLICATION

This is a national phase application based on the PCT International Patent Application No. PCT/JP2013/051911 filed Jan. 29, 2013, the entire contents of which are incorporated herein by reference.

TECHNICAL FIELD

The present invention relates to a control system of an internal combustion engine which controls an internal combustion engine in accordance with the output of an air-fuel ratio sensor.

BACKGROUND ART

In the past, a control system of an internal combustion engine which is provided with an air-fuel ratio sensor at an exhaust passage of the internal combustion engine and controls the amount of fuel fed to the internal combustion engine based on the output of this air-fuel ratio sensor, has been widely known (for example, see PLTs 1 to 4).

In such a control system, an exhaust purification catalyst which is provided in the exhaust passage and has an oxygen storage ability is used. An exhaust purification catalyst which has an oxygen storage ability can remove the unburned gas (HC, CO, etc.), $NO_x$, etc., in the exhaust gas flowing into the exhaust purification catalyst, when the oxygen storage amount is a suitable amount between an upper limit storage amount and a lower limit storage amount. That is, if exhaust gas of an air-fuel ratio at a rich side from the stoichiometric air-fuel ratio (below, also called a "rich air-fuel ratio") flows into the exhaust purification catalyst, the unburned gas in the exhaust gas is oxidized and purified by the oxygen stored in the exhaust purification catalyst. Conversely, if exhaust gas of an air-fuel ratio at a lean side from the stoichiometric air-fuel ratio (below, also called a "lean air-fuel ratio") flows into the exhaust purification catalyst, the oxygen in the exhaust gas is stored in the exhaust purification catalyst. Due to this, the surface of the exhaust purification catalyst becomes an oxygen deficient state. Therefore, the $NO_x$ in the exhaust gas is reduced and purified. As a result, the exhaust purification catalyst can purify the exhaust gas regardless of the air-fuel ratio of the exhaust gas flowing into the exhaust purification catalyst so long as the oxygen storage amount is a suitable amount.

Therefore, to maintain the oxygen storage amount in the exhaust purification catalyst at a suitable amount, the above control system is provided with an air-fuel ratio sensor at the upstream side of the exhaust purification catalyst in the direction of flow of exhaust and is provided with an oxygen sensor at the downstream side in the direction of flow of exhaust. By using these sensors, the control system performs feedback control based on the output of the upstream side air-fuel ratio sensor so that the output of this air-fuel ratio sensor becomes a target value which corresponds to a target air-fuel ratio. In addition, a target value of the upstream side air-fuel ratio sensor is corrected based on the output of the downstream side oxygen sensor. Note that, in the following explanation, the upstream side in the direction of flow of exhaust will sometimes simply be referred to as the "upstream side", and the downstream side in the direction of flow of exhaust will sometimes simply be referred to as the "downstream side".

For example, in the control system described in PLT 1, when the output voltage of the downstream side oxygen sensor is a high side threshold value or more and thus the state of the exhaust purification catalyst is an oxygen deficient state, the target air-fuel ratio of the exhaust gas flowing into the exhaust purification catalyst is set to a lean air-fuel ratio. Conversely, when the output voltage of the downstream side oxygen sensor is the low side threshold value or less and thus the state of the exhaust purification catalyst is an oxygen excess state, the target air-fuel ratio is set to the rich air-fuel ratio. According to PLT 1, due to this, when in the oxygen deficient state or oxygen excess state, it is considered that the state of the exhaust purification catalyst can be quickly returned to an intermediate state between these two states (that is, a state where the exhaust purification catalyst stores a suitable amount of oxygen).

In addition, in the above control system, if the output voltage of the downstream side oxygen sensor is between the high side threshold value and the low side threshold value, when the output voltage of the oxygen sensor tends to increase, the target air-fuel ratio is set to the lean air-fuel ratio. Conversely, when the output voltage of the oxygen sensor tends to decrease, the target air-fuel ratio is set to the rich air-fuel ratio. According to PLT 1, due to this, it is considered possible to prevent in advance the state of the exhaust purification catalyst from becoming an oxygen deficient state or oxygen excess state.

Further, in the control system described in PLT 2, the oxygen storage amount of the exhaust purification catalyst is calculated based on the outputs of the air flow meter and upstream side air-fuel ratio sensor of the exhaust purification catalyst. Moreover, when the calculated oxygen storage amount is larger than the target oxygen storage amount, the target air-fuel ratio of the exhaust gas flowing into the exhaust purification catalyst is set to the rich air-fuel ratio, while when the calculated oxygen storage amount is smaller than the target oxygen storage amount, the target air-fuel ratio is set to the lean air-fuel ratio. According to PLT 2, due to this, it is considered possible to constantly maintain the oxygen storage amount of the exhaust purification catalyst at the target oxygen storage amount.

CITATIONS LIST

Patent Literature

PLT 1: Japanese Patent Publication No. 2011-069337 A
PLT 2: Japanese Patent Publication No. 2001-234787 A
PLT 3: Japanese Patent Publication No. H8-232723 A
PLT 4: Japanese Patent Publication No. 2009-162139 A

SUMMARY OF INVENTION

Technical Problem

FIG. 2 shows the relationship between the oxygen storage amount of the exhaust purification catalyst and the concentration of $NO_x$ or unburned gas (HC, CO, etc.) of the exhaust gas flowing out from the exhaust purification catalyst. FIG. 2(A) shows the relationship between the oxygen storage amount and the $NO_x$ concentration in the exhaust gas flowing out from the exhaust purification catalyst, when the air-fuel ratio of the exhaust gas flowing into the exhaust purification catalyst is the lean air-fuel ratio. On the other hand, FIG. 2(B) shows the relationship between the oxygen storage amount and the concentration of unburned gas in the exhaust gas flowing out from the exhaust purification catalyst, when the air-fuel ratio of the exhaust gas flowing into the exhaust purification catalyst is the rich air-fuel ratio.

As will be understood from FIG. 2(A), when the oxygen storage amount of the exhaust purification catalyst is small, there is leeway until the maximum oxygen storage amount. Therefore, even when the air-fuel ratio of the exhaust gas flowing into the exhaust purification catalyst is the lean air-fuel ratio (that is, this exhaust gas includes $NO_x$ and oxygen), the oxygen in the exhaust gas is stored in the exhaust purification catalyst. Along with this, $NO_x$ is reduced and purified. As a result, the exhaust gas flowing out from the exhaust purification catalyst does not contain much $NO_x$ at all.

However, if the oxygen storage amount of the exhaust purification catalyst becomes greater, when the air-fuel ratio of the exhaust gas flowing into the exhaust purification catalyst is the lean air-fuel ratio, it becomes harder to store the oxygen in the exhaust gas, in the exhaust purification catalyst. Along with this, it becomes harder for the $NO_x$ in the exhaust gas to also be reduced and purified. Therefore, as will be understood from FIG. 2(A), if the oxygen storage amount increases beyond a certain upper limit storage amount Cuplim, the concentration of $NO_x$ in the exhaust gas flowing out from the exhaust purification catalyst rapidly rises.

On the other hand, when the oxygen storage amount of the exhaust purification catalyst is large, if the air-fuel ratio of the exhaust gas flowing into the exhaust purification catalyst is the rich air-fuel ratio (that is, this exhaust gas includes HC or CO or other unburned gas), the oxygen stored in the exhaust purification catalyst is released. Therefore, the unburned gas in the exhaust gas flowing into the exhaust purification catalyst is oxidized and purified. As a result, as will be understood from FIG. 2(B), the exhaust gas flowing out from the exhaust purification catalyst does not contain almost any unburned gas as well.

However, if the oxygen storage amount of the exhaust purification catalyst becomes smaller, when the air-fuel ratio of the exhaust gas flowing into the exhaust purification catalyst is a rich air-fuel ratio, the oxygen released from the exhaust purification catalyst becomes smaller. Along with this, it is more difficult for the unburned gas in the exhaust gas to be oxidized and purified. Therefore, as will be understood from FIG. 2(B), if the oxygen storage amount decreases over a certain lower limit storage amount Clowlim, the concentration of the unburned gas in the exhaust gas flowing out from the exhaust purification catalyst rapidly rises.

The oxygen storage amount of the exhaust purification catalyst and the $NO_x$ concentration in the outflowing exhaust gas have the above-mentioned relationship. Therefore, when performing the control described in PLT 1, that is, when performing control which sets the target air-fuel ratio to the rich air-fuel ratio when the output voltage of the downstream side oxygen sensor becomes the low side threshold value or less, a certain extent of $NO_x$ flows out from the exhaust purification catalyst. This state is shown in FIG. 20.

FIG. 20 is a time chart of the oxygen storage amount of the exhaust purification catalyst, the air-fuel ratio of the exhaust gas detected by the downstream side oxygen sensor, the target air-fuel ratio of the exhaust gas flowing into the exhaust purification catalyst, the air-fuel ratio of the exhaust gas detected by the upstream side oxygen sensor, and the $NO_x$ concentration in the exhaust gas flowing out from the exhaust purification catalyst.

In the illustrated example, in the state before the time $t_1$, the target air-fuel ratio of the exhaust gas flowing into the exhaust purification catalyst is set to the lean air-fuel ratio. Therefore, the oxygen storage amount of the exhaust purification catalyst gradually increases. On the other hand, the oxygen in the exhaust gas flowing into the exhaust purification catalyst is completely stored in the exhaust purification catalyst, therefore the exhaust gas flowing out from the exhaust purification catalyst does not contain almost any oxygen.

Therefore, the air-fuel ratio of the exhaust gas detected by the downstream side oxygen sensor becomes substantially the stoichiometric air-fuel ratio. Similarly, the $NO_x$ in exhaust gas flowing into the exhaust purification catalyst is completely reduced and purified at the exhaust purification catalyst, and therefore the exhaust gas flowing out from the exhaust purification catalyst does not contain almost any $NO_x$.

If the oxygen storage amount of the exhaust purification catalyst gradually increases and approaches the maximum oxygen storage amount Cmax, as shown in FIG. 2, part of the oxygen in the exhaust gas flowing into the exhaust purification catalyst can no longer be stored in the exhaust purification catalyst. As a result, from the time $t_1$, the exhaust gas flowing out from the exhaust purification catalyst contains oxygen. Therefore, the air-fuel ratio of the exhaust gas detected by the downstream side oxygen sensor becomes the lean air-fuel ratio. Then, if the oxygen storage amount of the exhaust purification catalyst further increases, the air-fuel ratio of the exhaust gas flowing out from the exhaust purification catalyst reaches a predetermined upper limit air-fuel ratio AFhighref (corresponding to low side threshold value) and the target air-fuel ratio is switched to the rich air-fuel ratio.

If the target air-fuel ratio is switched to the rich air-fuel ratio, the fuel injection amount at the internal combustion engine is increased in accordance with the switched target air-fuel ratio. Even if the fuel injection amount is increased in this way, since there is a certain extent of distance from the internal combustion engine body to the exhaust purification catalyst, the air-fuel ratio of the exhaust gas flowing into the exhaust purification catalyst is not immediately changed to the rich air-fuel ratio but is delayed. Therefore, even if the target air-fuel ratio is switched at the time $t_2$ to the rich air-fuel ratio, up to the time $t_3$, the air-fuel ratio of the exhaust gas flowing into the exhaust purification catalyst remains at the lean air-fuel ratio. Therefore, from the time $t_2$ to $t_3$, the oxygen storage amount of the exhaust purification catalyst reaches the maximum oxygen storage amount Cmax or becomes a value near the maximum oxygen storage amount Cmax. As a result, oxygen and $NO_x$ flow out from the exhaust purification catalyst. Then, at the time $t_3$, the air-fuel ratio of the exhaust gas flowing into the exhaust purification catalyst becomes the rich air-fuel ratio and the air-fuel ratio of the exhaust gas flowing out from the exhaust purification catalyst converges to the stoichiometric air-fuel ratio.

In this way, even if performing the control described in PLT 1, a delay occurs from when switching the target air-fuel ratio to when the air-fuel ratio of the exhaust gas flowing into the exhaust purification catalyst becomes the rich air-fuel ratio. As a result, as will be understood from the "$NO_x$ concentration in outflowing gas" in FIG. 20, $NO_x$ temporarily flows out from the exhaust purification catalyst.

Further, when calculating the estimated value of the oxygen storage amount of the exhaust purification catalyst, based on the outputs of the air flow meter and upstream side air-fuel ratio sensor, etc., as shown in the control system which is described in PLT 2, error occurs in the estimated value. Such error is large if calculating the estimated value of the oxygen storage amount by accumulating the outputs over a long time period, even if such error is small if calculating it in a short time period. As a result, even if controlling the air-fuel ratio of the exhaust gas flowing into the exhaust purification catalyst so that the actual oxygen storage amount becomes the target oxygen storage amount, the oxygen storage amount of the exhaust purification catalyst finally reaches the maximum oxygen storage amount or zero.

In the control system described in PLT 2, envisioning such a situation, when the downstream side oxygen sensor detects an air-fuel ratio other than the stoichiometric air-fuel ratio, the estimated value of the oxygen storage amount is corrected to return the actual oxygen storage amount to a suitable amount. However, in this case as well, a delay occurs from when the estimated value of the oxygen storage amount is corrected to when this is reflected into the air-fuel ratio of the exhaust gas flowing into the exhaust purification catalyst. As a result, similarly to the control system described in PLT 1, $NO_x$ temporarily flows out from the exhaust purification catalyst.

Therefore, in consideration of the above problem, an object of the present invention is to provide a control system of an internal combustion engine comprising an exhaust purification catalyst which has an oxygen storage ability, wherein the control system keeps the oxygen storage amount of the exhaust purification catalyst from reaching the maximum oxygen storage amount and $NO_x$ from remaining in the exhaust gas flowing out from the exhaust purification catalyst.

Solution to Problem

To solve the above problem, in a first aspect of the invention, there is provided a control system of an internal combustion engine, the engine comprising an exhaust purification catalyst which is arranged in an exhaust passage of the internal combustion engine and which can store oxygen, the control system comprising: a downstream side air-fuel ratio detecting means which is arranged at the downstream side, in the direction of flow of exhaust, from the exhaust purification catalyst and which detects an air-fuel ratio of exhaust gas flowing out from the exhaust purification catalyst; and an inflowing air-fuel ratio control means which control an air-fuel ratio of exhaust gas flowing into the exhaust purification catalyst, wherein the inflowing air-fuel ratio control means comprises: an oxygen storage amount increasing means for continuously or intermittently setting a target air-fuel ratio of exhaust gas flowing into the exhaust purification catalyst to leaner than the stoichiometric air-fuel ratio, when the air-fuel ratio detected by the downstream side air-fuel ratio detecting means becomes a rich judged air-fuel ratio, which is richer than the stoichiometric air-fuel ratio, or less, until the oxygen storage amount of the exhaust purification catalyst becomes a given storage amount which is smaller than an upper limit oxygen storage amount where the rates of rise of the concentrations of the oxygen and $NO_X$ in the exhaust gas flowing out from the exhaust purification catalyst start to become higher than before; and an oxygen storage amount decreasing means for continuously or intermittently setting the target air-fuel ratio to richer than the stoichiometric air-fuel ratio, when the oxygen storage amount of the exhaust purification catalyst becomes the given storage amount or more, so that the oxygen storage amount decreases toward zero without reaching the maximum oxygen storage amount.

To solve the above problem, in a first aspect of the invention, there is provided a control system of internal combustion engine, the engine comprising an exhaust purification catalyst which is arranged in an exhaust passage of the internal combustion engine and which can store oxygen, the control system comprising: a downstream side air-fuel ratio detecting means which is arranged at a downstream side, in a direction of flow of exhaust, from the exhaust purification catalyst and which detects air-fuel ratio of the exhaust gas flowing out from the exhaust purification catalyst; an inflowing air-fuel ratio control means which controls the air-fuel ratio of the exhaust gas flowing into the exhaust purification catalyst; an upstream side air-fuel ratio detecting/estimating means which detects or estimates the air-fuel ratio of the exhaust gas flowing into the exhaust purification catalyst; and an oxygen storage amount estimating means which estimates an oxygen storage amount of the exhaust purification catalyst based on the air-fuel ratio of the exhaust gas which is detected or estimated by the upstream side air-fuel ratio detecting/estimating means, wherein the inflowing air-fuel ratio control means comprises: an oxygen storage amount increasing means for continuously or intermittently setting a target air-fuel ratio of the exhaust gas flowing into the exhaust purification catalyst to leaner than the stoichiometric air-fuel ratio, when the air-fuel ratio detected by the downstream side air-fuel ratio detecting means becomes a rich judged air-fuel ratio, which is richer than the stoichiometric air-fuel ratio, or less, until the oxygen storage amount which is estimated by the oxygen storage amount estimating means becomes a given storage amount which is smaller than the maximum oxygen storage amount; and an oxygen storage amount decreasing means for continuously or intermittently setting the target air-fuel ratio to richer than the stoichiometric air-fuel ratio, when the oxygen storage amount which is estimated by the oxygen storage amount estimating means becomes the given storage amount or more, so that the oxygen storage amount decreases toward zero without reaching the maximum oxygen storage amount.

In a third aspect of the invention, there is provided the first or second aspect of the invention, wherein a difference between an average value of the target air-fuel ratio and the stoichiometric air-fuel ratio in the time period when the target air-fuel ratio is continuously or intermittently set to leaner than the stoichiometric air-fuel ratio by the oxygen storage amount increasing means is larger than a difference between an average value of the target air-fuel ratio and the stoichiometric air-fuel ratio in the time period when the target air-fuel ratio is continuously or intermittently set to richer than the stoichiometric air-fuel ratio by the oxygen storage amount decreasing means.

In a fourth aspect of the invention, there is provided any one of the first to third aspects of the invention, wherein the oxygen storage amount increasing means continuously maintains the target air-fuel ratio leaner than the stoichiometric air-fuel ratio.

In a fifth aspect of the invention, there is provided any one of the first to fourth aspects of the invention, wherein the oxygen storage amount decreasing means continuously maintains the target air-fuel ratio richer than the stoichiometric air-fuel ratio.

In a sixth aspect of the invention, there is provided any one of the first to third aspects of the invention, wherein the oxygen storage amount decreasing means intermittently set the target air-fuel ratio to richer than the stoichiometric air-fuel ratio, and set the target air-fuel ratio to leaner than the stoichiometric air-fuel ratio in at least a part of a time period when the target air-fuel ratio is not set to the stoichmetric air-fuel ratio.

In a seventh aspect of the invention, there is provided any one of the first to sixth aspects of the invention, further comprising an upstream side air-fuel ratio detecting/estimating means which detects or estimates the air-fuel ratio of the exhaust gas flowing into the exhaust purification catalyst, wherein the inflowing air-fuel ratio control means controls an amount of fuel supplied into a combustion chamber of the internal combustion engine so that the air-fuel ratio of the exhaust gas, which is detected or estimated by the upstream side air-fuel ratio detecting/estimating means, becomes the target air-fuel ratio.

In an eighth aspect of the invention, there is provided the seventh aspect of the invention, further comprising an oxygen storage amount estimating means which estimates an oxygen storage amount of the exhaust purification catalyst based on the air-fuel ratio of the exhaust gas detected or estimated by the upstream side air-fuel ratio detecting/estimating means, wherein the oxygen storage amount increasing means sets the target air-fuel ratio to leaner than the stoichiometric air-fuel ratio until the oxygen storage amount estimated by the oxygen storage amount estimating means becomes the given storage amount.

In a ninth aspect of the invention, there is provided any one of the first to eighth aspects of the invention, wherein the internal combustion engine further comprises a downstream side exhaust purification catalyst which is arranged in the exhaust passage at the downstream side, in the direction of flow of exhaust, from the downstream side air-fuel ratio detecting means and which can store oxygen.

In a 10th aspect of the invention, there is provided any one of the first to ninth aspects of the invention, wherein the the operation based on storage amount increasing means and the operation based on the storage amount decreasing means are alternatively and repeatedly performed.

Advantageous Effects of Invention

According to the present invention, the oxygen storage amount of the exhaust purification catalyst is kept from reaching the maximum oxygen storage amount and $NO_x$ is kept from remaining in the exhaust gas flowing out from the exhaust purification catalyst, in an internal combustion engine comprising an exhaust purification catalyst which has an oxygen storage ability.

DESCRIPTION OF EMBODIMENTS

Figure 1:
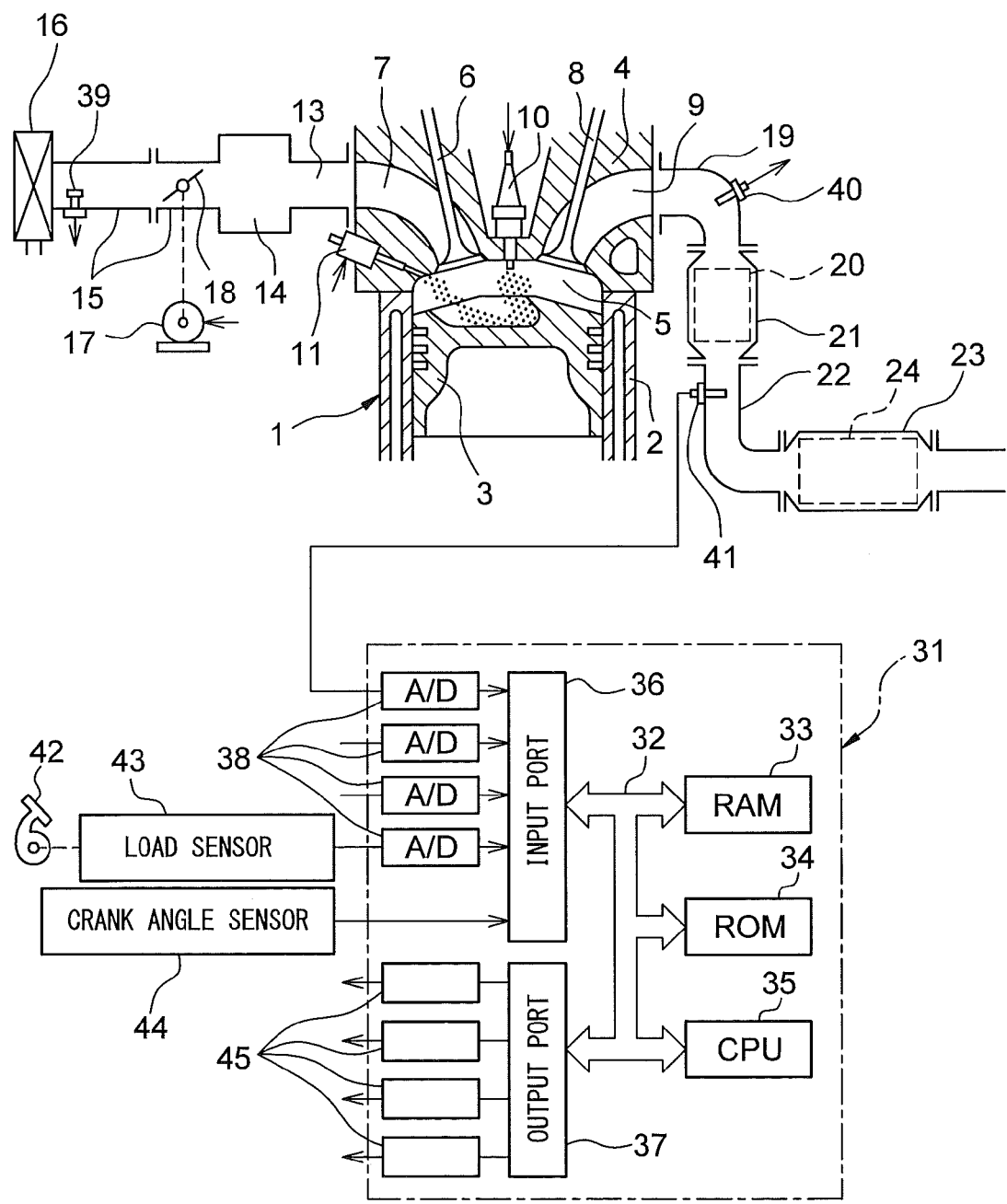
FIG. 1 is a view which schematically shows an internal combustion engine in which a control system of the present invention is used.

Below, referring to the drawings, a control device of an internal combustion engine of the present invention will be explained in detail. Note that, in the following explanation, similar component elements are assigned the same reference numerals. FIG. 1 is a view which schematically shows an internal combustion engine in which a control device according to a first embodiment of the present invention is used.

<Explanation of Internal Combustion Engine as a Whole>

Referring to FIG. 1, 1 indicates an engine body, 2 a cylinder block, 3 a piston which reciprocates inside the cylinder block 2, 4 a cylinder head which is fastened to the cylinder block 2, 5 a combustion chamber which is formed between the piston 3 and the cylinder head 4, 6 an intake valve, 7 an intake port, 8 an exhaust valve, and 9 an exhaust port. The intake valve 6 opens and closes the intake port 7, while the exhaust valve 8 opens and closes the exhaust port 9.

As shown in FIG. 1, a spark plug 10 is arranged at a center part of an inside wall surface of the cylinder head 4, while a fuel injector 11 is arranged at a side part of the inner wall surface of the cylinder head 4. The spark plug 10 is configured to generate a spark in accordance with an ignition signal. Further, the fuel injector 11 injects a predetermined amount of fuel into the combustion chamber 5 in accordance with an injection signal. Note that, the fuel injector 11 may also be arranged so as to inject fuel into the intake port 7.

Further, in the present embodiment, as the fuel, gasoline with a stoichiometric air-fuel ratio of 14.6 at an exhaust purification catalyst is used. However, the internal combustion engine of the present invention may also use another fuel.

The intake port 7 of each cylinder is connected to a surge tank 14 through a corresponding intake branch pipe 13, while the surge tank 14 is connected to an air cleaner 16 through an intake pipe 15. The intake port 7, intake branch pipe 13, surge tank 14, and intake pipe 15 form an intake passage. Further, inside the intake pipe 15, a throttle valve 18 which is driven by a throttle valve drive actuator 17 is arranged. The throttle valve 18 can be operated by the throttle valve drive actuator 17 to thereby change the aperture area of the intake passage.

On the other hand, the exhaust port 9 of each cylinder is connected to an exhaust manifold 19. The exhaust manifold 19 has a plurality of branch pipes which are connected to the exhaust ports 9 and a header at which these branch pipes are collected. The header of the exhaust manifold 19 is connected to an upstream side casing 21 which houses an upstream side exhaust purification catalyst 20. The upstream side casing 21 is connected through an exhaust pipe 22 to a downstream side casing 23 which houses a downstream side exhaust purification catalyst 24. The exhaust port 9, exhaust manifold 19, upstream side casing 21, exhaust pipe 22, and downstream side casing 23 form an exhaust passage.

The electronic control unit (ECU) 31 is comprised of a digital computer which is provided with components which are connected together through a bidirectional bus 32 such as a RAM (random access memory) 33, ROM (read only memory) 34, CPU (microprocessor) 35, input port 36, and output port 37. In the intake pipe 15, an air flow meter 39 is arranged for detecting the flow rate of air flowing through the intake pipe 15. The output of this air flow meter 39 is input through a corresponding AD converter 38 to the input port 36. Further, at the header of the exhaust manifold 19, an upstream side air-fuel ratio sensor (upstream side air-fuel ratio detection means) 40 is arranged which detects the air-fuel ratio of the exhaust gas flowing through the inside of the exhaust manifold 19 (that is, the exhaust gas flowing into the upstream side exhaust purification catalyst 20). In addition, in the exhaust pipe 22, a downstream side air-fuel ratio sensor (downstream side air-fuel ratio detection means) 41 is arranged which detects the air-fuel ratio of the exhaust gas flowing through the inside of the exhaust pipe 22 (that is, the exhaust gas flowing out from the upstream side exhaust purification catalyst 20 and flows into the downstream side exhaust purification catalyst 24). The outputs of these air-fuel ratio sensors 40 and 41 are also input through the corresponding AD converters 38 to the input port 36. Note that, the configurations of these air-fuel ratio sensors 40 and 41 will be explained later.

Further, an accelerator pedal 42 has a load sensor 43 connected to it which generates an output voltage which is proportional to the amount of depression of the accelerator pedal 42. The output voltage of the load sensor 43 is input to the input port 36 through a corresponding AD converter 38. The crank angle sensor 44 generates an output pulse every time, for example, a crankshaft rotates by 15 degrees. This output pulse is input to the input port 36. The CPU 35 calculates the engine speed from the output pulse of this crank angle sensor 44. On the other hand, the output port 37 is connected through corresponding drive circuits 45 to the spark plugs 10, fuel injectors 11, and throttle valve drive actuator 17. Note that the ECU 31 functions as control means for controlling the internal combustion engine based on the outputs of various sensors, etc.

<Explanation of Exhaust Purification Catalyst>

The upstream side exhaust purification catalyst 20 and the downstream side exhaust purification catalyst 24 both have similar configurations. Below, only the upstream side exhaust purification catalyst 20 will be explained, but the downstream side exhaust purification catalyst 24 may also have a similar configuration and action.

The upstream side exhaust purification catalyst 20 is a three-way catalyst which has an oxygen storage ability. Specifically, the upstream side exhaust purification catalyst 20 is comprised of a carrier made of ceramic on which a precious metal which has a catalytic action (for example, platinum (Pt)) and a substance which has an oxygen storage ability (for example, ceria ($CeO_2$)) are carried. If the upstream side exhaust purification catalyst 20 reaches a predetermined activation temperature, it exhibits an oxygen storage ability in addition to the catalytic action of simultaneously removing the unburned gas (HC, CO, etc.) and nitrogen oxides ($NO_x$).

According to the oxygen storage ability of the upstream side exhaust purification catalyst 20, the upstream side exhaust purification catalyst 20 stores the oxygen in the exhaust gas, when the air-fuel ratio of the exhaust gas flowing into the upstream side exhaust purification catalyst 20 is leaner than the stoichiometric air-fuel ratio (lean air-fuel ratio). On the other hand, the upstream side exhaust purification catalyst 20 releases the oxygen which is stored in the upstream side exhaust purification catalyst 20 when the air-fuel ratio of the inflowing exhaust gas is richer than the stoichiometric air-fuel ratio (rich air-fuel ratio). Note that, the "air-fuel ratio of the exhaust gas" means the ratio of the mass of the air to the mass of the fuel which are fed up to when the exhaust gas is produced. Usually, it means the ratio of the mass of the air to the mass of the fuel which are fed into the combustion chamber 5 when that exhaust gas is produced. Note that in the present specification, an air-fuel ratio of exhaust gas may be referred to as "exhaust air-fuel ratio".

Figure 2:
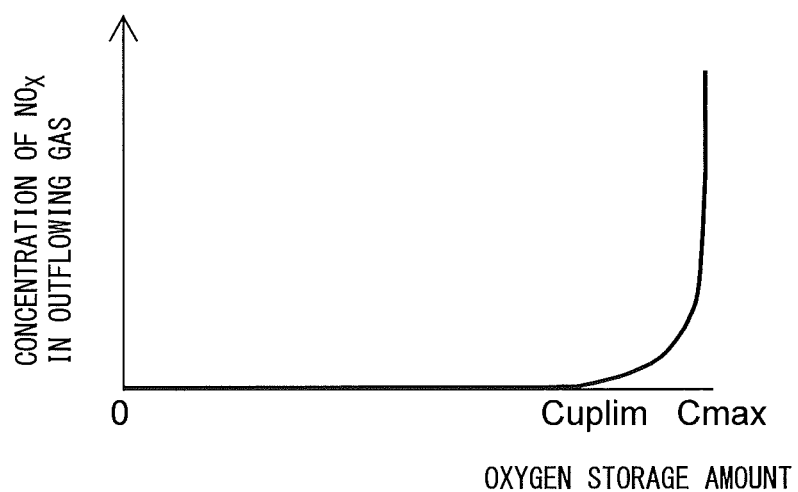
FIG. 2 is a view which shows the relationship between the oxygen storage amount of an exhaust purification catalyst and a concentration of $NO_x$ or unburned gas in exhaust gas flowing out from an exhaust purification catalyst.
Figure 2:
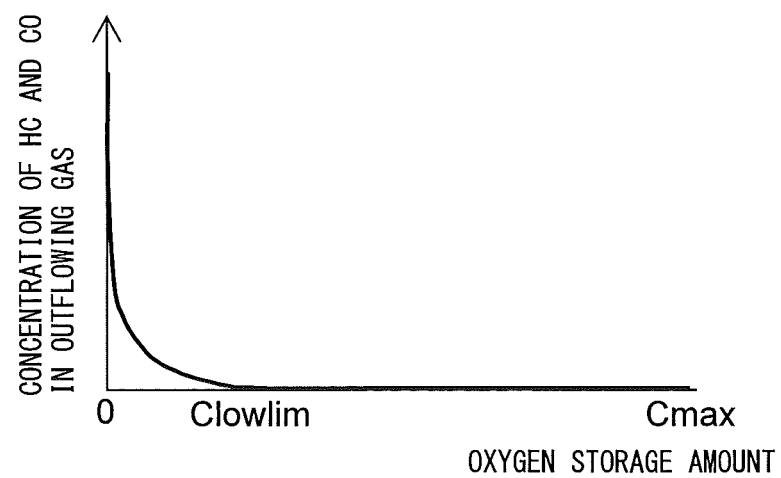

The upstream side exhaust purification catalyst 20 has a catalytic action and oxygen storage ability and thereby has the purifying function of the $NO_x$ and unburned gas in accordance with the oxygen storage amount. That is, as shown in FIG. 2(A), if the air-fuel ratio of the exhaust gas flowing into the upstream side exhaust purification catalyst 20 is the lean air-fuel ratio, when the oxygen storage amount is small, the upstream side exhaust purification catalyst 20 stores the oxygen in the exhaust gas, and reduces and purifies the $NO_x$. Further, if the oxygen storage amount becomes greater, the concentrations of the oxygen and $NO_x$ in the exhaust gas flowing out from the upstream side exhaust purification catalyst 20 rapidly rises starting from the upper limit storage amount Cuplim.

On the other hand, as shown in FIG. 2(B), if the air-fuel ratio of the exhaust gas flowing into the upstream side exhaust purification catalyst 20 is the rich air-fuel ratio, when the oxygen storage amount is large, the oxygen which is stored in the upstream side exhaust purification catalyst 20 is released and the unburned gas in the exhaust gas is oxidized and purified. Further, if the oxygen storage amount becomes small, the concentration of the unburned gas in the exhaust gas flowing out from the upstream side exhaust purification catalyst 20 rapidly rises starting from the lower limit storage amount Clowlim.

As mentioned above, according to the exhaust purification catalysts 20, 24 used in the present embodiment, the characteristic of purification of $NO_x$ and unburned gas in the exhaust gas changes in accordance with the air-fuel ratio of the exhaust gas flowing into the exhaust purification catalysts 20, 24 and oxygen storage amount. Note that, as long as the exhaust purification catalysts 20, 24 has a catalytic function and oxygen storage ability, the exhaust purification catalysts 20, 24 may also be catalysts which are different from three-way catalysts.

<Configuration of Air-Fuel Ratio Sensor>

Figure 3:
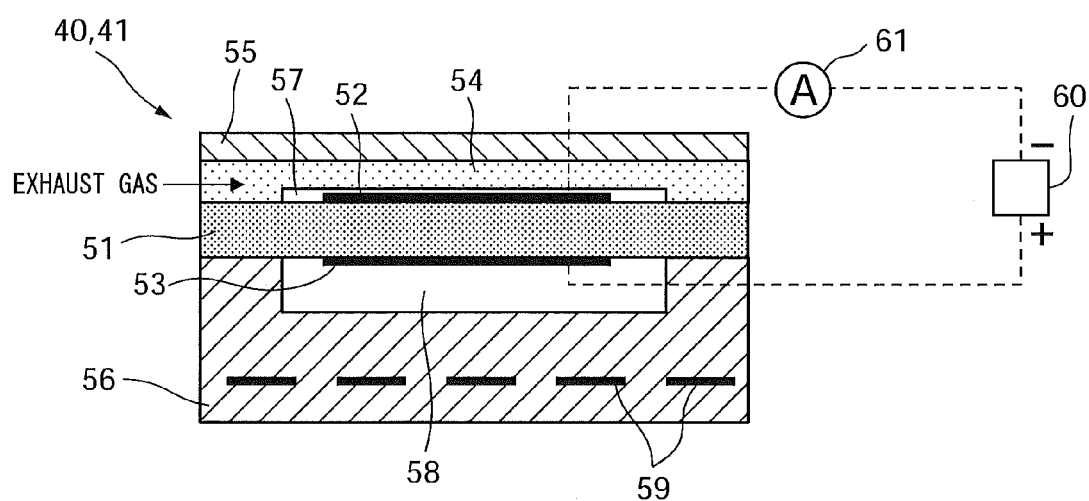
FIG. 3 is a schematic cross-sectional view of an air-fuel ratio sensor.

Next, referring to FIG. 3, the configurations of air-fuel ratio sensors 40 and 41 in the present embodiment will be explained. FIG. 3 is a schematic cross-sectional view of air-fuel ratio sensors 40 and 41. As will be understood from FIG. 3, the air-fuel ratio sensors 40 and 41 in the present embodiment are single-cell type air-fuel ratio sensors each comprised of a solid electrolyte layer and a pair of electrodes forming a single cell.

As shown in FIG. 3, each of the air-fuel ratio sensors 40 and 41 is provided with a solid electrolyte layer 51, an exhaust side electrode (first electrode) 52 which is arranged at one lateral surface of the solid electrolyte layer 51, an atmosphere side electrode (second electrode) 53 which is arranged at the other lateral surface of the solid electrolyte layer 51, a diffusion regulation layer 54 which regulates the diffusion of the passing exhaust gas, a protective layer 55 which protects the diffusion regulation layer 54, and a heater part 56 which heats the air-fuel ratio sensor 40 or 41.

On one lateral surface of the solid electrolyte layer 51, a diffusion regulation layer 54 is provided. On the lateral surface of the diffusion regulation layer 54 at the opposite side from the lateral surface of the solid electrolyte layer 51 side, a protective layer 55 is provided. In the present embodiment, a measured gas chamber 57 is formed between the solid electrolyte layer 51 and the diffusion regulation layer 54. In this measured gas chamber 57, the gas to be detected by the air-fuel ratio sensors 40 and 41, that is, the exhaust gas, is introduced through the diffusion regulation layer 54. Further, the exhaust side electrode 52 is arranged inside the measured gas chamber 57, therefore, the exhaust side electrode 52 is exposed to the exhaust gas through the diffusion regulation layer 54. Note that, the measured gas chamber 57 does not necessarily have to be provided. The diffusion regulation layer 54 may directly contact the surface of the exhaust side electrode 52.

On the other lateral surface of the solid electrolyte layer 51, the heater part 56 is provided. Between the solid electrolyte layer 51 and the heater part 56, a reference gas chamber 58 is formed. Inside this reference gas chamber 58, a reference gas is introduced. In the present embodiment, the reference gas chamber 58 is open to the atmosphere. Therefore, inside the reference gas chamber 58, the atmosphere is introduced as the reference gas. The atmosphere side electrode 53 is arranged inside the reference gas chamber 58, therefore, the atmosphere side electrode 53 is exposed to the reference gas (reference atmosphere).). In the present embodiment, atmospheric air is used as the reference gas, so the atmosphere side electrode 53 is exposed to the atmosphere.

The heater part 56 is provided with a plurality of heaters 59. These heaters 59 can be used to control the temperature of the air-fuel ratio sensor 40 or 41, in particular, the temperature of the solid electrolyte layers 51. The heater part 56 has a sufficient heat generation capacity for heating the solid electrolyte layer 51 until activating.

The solid electrolyte layer 51 is formed by a sintered body of $ZrO_2$ (zirconia), $HfO_2$, $ThO_2$, $Bi_2O_2$, or other oxygen ion conducting oxide in which CaO, MgO, $Y_2O_3$, $Yb_2O_2$, etc. is blended as a stabilizer. Further, the diffusion regulation layer 54 is formed by a porous sintered body of alumina, magnesia, silica, spinel, mullite, or another heat resistant inorganic substance. Furthermore, the exhaust side electrode 52 and atmosphere side electrode 53 is formed by platinum or other precious metal with a high catalytic activity.

Further, between the exhaust side electrode 52 and the atmosphere side electrode 53, sensor voltage Vr is supplied by the voltage application device 60 which is mounted on the ECU 31. In addition, the ECU 31 is provided with a current detection device 61 which detects the current which flows between these electrodes 52 and 53 through the solid electrolyte layer 51 when the voltage application device 60 supplies the sensor voltage Vr. The current which is detected by this current detection device 61 is the output current of the air-fuel ratio sensors 40 and 41.

<Operation of Air-Fuel Ratio Sensor>

Figure 4:
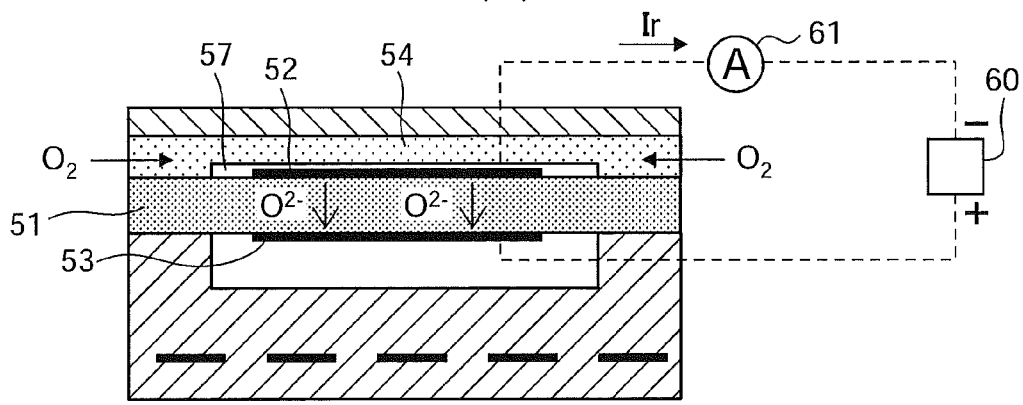
FIG. 4 is a view which schematically shows an operation of an air-fuel ratio sensor.
Figure 4:
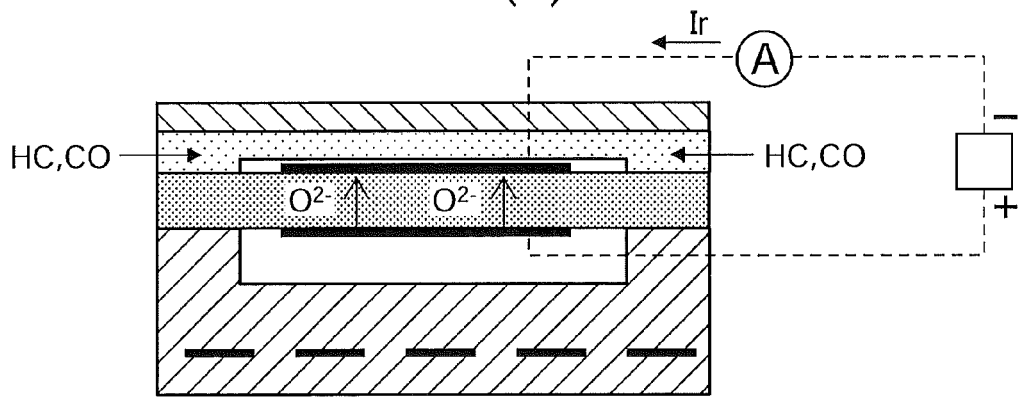
Figure 4:
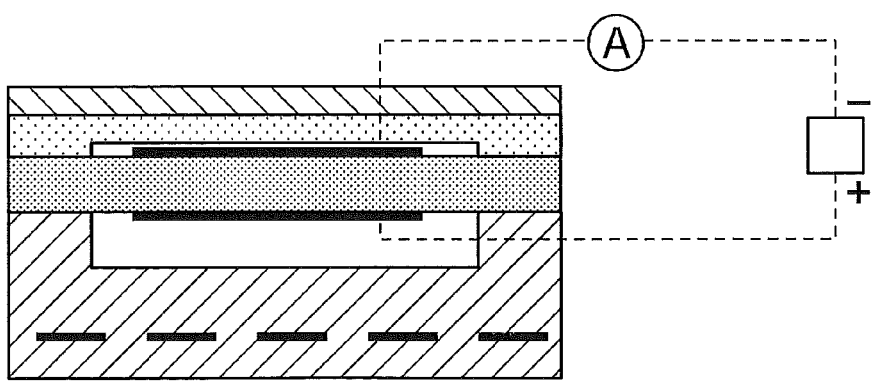

Next, referring to FIG. 4, the basic concept of the operation of the thus configured air-fuel ratio sensors 40, 41 will be explained. FIG. 4 is a view which schematically shows the operation of the air-fuel ratio sensors 40, 41. At the time of use, each of the air-fuel ratio sensors 40, 41 is arranged so that the protection layer 55 and the outer circumferential surface of the diffusion regulating layer 54 are exposed to the exhaust gas. Further, atmospheric air is introduced into the reference gas chamber 58 of the air-fuel ratio sensors 40, 41.

In the above-mentioned way, the solid electrolyte layer 51 is formed by a sintered body of an oxygen ion conductive oxide. Therefore, it has the property of an electromotive force E being generated which makes oxygen ions move from the high concentration lateral surface side to the low concentration lateral surface side if a difference occurs in the oxygen concentration between the two lateral surfaces of the solid electrolyte layer 51 in the state activated by the high temperature (oxygen cell characteristic).

Conversely, if a potential difference occurs between the two lateral surfaces, the solid electrolyte layer 51 has the characteristic of trying to make the oxygen ions move so that a ratio of oxygen concentration occurs between the two lateral surfaces of the solid electrolyte layer in accordance with the potential difference (oxygen pump characteristic). Specifically, when a potential difference occurs across the two lateral surfaces, movement of oxygen ions is caused so that the oxygen concentration at the lateral surface which has a positive polarity becomes higher than the oxygen concentration at the lateral surface which has a negative polarity, by a ratio according to the potential difference. Further, as shown in FIGS. 3 and 4, in the air-fuel ratio sensors 40, 41, a constant sensor applied voltage Vr is applied across electrodes 52, 53 so that the atmosphere side electrode 53 becomes the positive electrode and the exhaust side electrode 52 becomes the negative electrode. Note that, in the present embodiment, the sensor applied voltages Vr in the air-fuel ratio sensors 40 and 41 are the same voltage as each other.

When the exhaust air-fuel ratio around the air-fuel ratio sensors 40, 41 is leaner than the stoichiometric air-fuel ratio, the ratio of the oxygen concentrations between the two lateral surfaces of the solid electrolyte layer 51 does not become that large. Therefore, if setting the sensor applied voltage Vr at a suitable value, between the two lateral surfaces of the solid electrolyte layer 51, the actual oxygen concentration ratio becomes smaller than the oxygen concentration ratio corresponding to the sensor applied voltage Vr. For this reason, the oxygen ions move from the exhaust side electrode 52 toward the atmosphere side electrode 43 as shown in FIG. 4(A) so that the oxygen concentration ratio between the two lateral surfaces of the solid electrolyte layer 51 becomes larger toward the oxygen concentration ratio corresponding to the sensor applied voltage Vr. As a result, current flows from the positive side of the voltage application device 60 which applies the sensor applied voltage Vr, through the atmosphere side electrode 53, solid electrolyte layer 51, and exhaust side electrode 52, to the negative side of the voltage application device 60.

The magnitude of the current (output current) Ir flowing at this time is proportional to the amount of oxygen flowing by diffusing from the exhaust through the diffusion regulating layer 54 to the measured gas chamber 57, if setting the sensor applied voltage Vr to a suitable value. Therefore, by detecting the magnitude of this current Ir by the current detection device 61, it is possible to learn the oxygen concentration and in turn possible to learn the air-fuel ratio in the lean region.

On the other hand, when the exhaust air-fuel ratio around the air-fuel ratio sensors 40, 41 is richer than the stoichiometric air-fuel ratio, unburned gas flows in from the exhaust through the diffusion regulating layer 54 to the inside of the measured gas chamber 57, and therefore even if there is oxygen present on the exhaust side electrode 52, oxygen reacts with the unburned gas and is removed. Therefore, inside the measured gas chamber 57, the oxygen concentration becomes extremely low. As a result, the ratio of the oxygen concentration between the two lateral surfaces of the solid electrolyte layer 51 becomes large. For this reason, if setting the sensor applied voltage Vr to a suitable value, between the two lateral surfaces of the solid electrolyte layer 51, the actual oxygen concentration ratio will become larger than the oxygen concentration ratio corresponding to the sensor applied voltage Vr. Therefore, as shown in FIG. 4(B), oxygen ions move from the atmosphere side electrode 53 toward the exhaust side electrode 52 so that the oxygen concentration ratio between the two lateral surfaces of the solid electrolyte layer 51 becomes smaller toward the oxygen concentration ratio corresponding to the sensor applied voltage Vr. As a result, current flows from the atmosphere side electrode 53, through the voltage application device 60 which applies the sensor applied voltage Vr, to the exhaust side electrode 52.

The magnitude of the current (output current) Ir flowing at this time is determined by the flow rate of oxygen ions which move through the solid electrolyte layer 51 from the atmosphere side electrode 53 to the exhaust side electrode 52, if setting the sensor applied voltage Vr to a suitable value. The oxygen ions react (burn) with the unburned gas, which diffuses from the exhaust through the diffusion regulating layer 54 to the measured gas chamber 57, on the exhaust side electrode 52. Accordingly, the flow rate in movement of the oxygen ions corresponds to the concentration of unburned gas in the exhaust gas flowing into the measured gas chamber 57. Therefore, by detecting the magnitude of this current Ir by the current detection device 61, it is possible to learn the concentration of unburned gas and in turn possible to learn the air-fuel ratio in the rich region.

Further, when the exhaust air-fuel ratio around the air-fuel ratio sensors 40, 41 is the stoichiometric air-fuel ratio, the amounts of oxygen and unburned gas which flow into the measured gas chamber 57 become a chemical equivalent ratio. Therefore, due to the catalytic action of the exhaust side electrode 52, oxygen and unburned gas completely burn and no fluctuation arises in the concentrations of oxygen and unburned gas in the measured gas chamber 57. As a result, the oxygen concentration ratio across the two lateral surfaces of the solid electrolyte layer 51 does not fluctuate, but is maintained at the oxygen concentration ratio corresponding to the sensor applied voltage Vr. For this reason, as shown in FIG. 4(C), no movement of oxygen ions occurs due to the oxygen pump characteristic. As a result, no current flows through the circuits.

Figure 5:
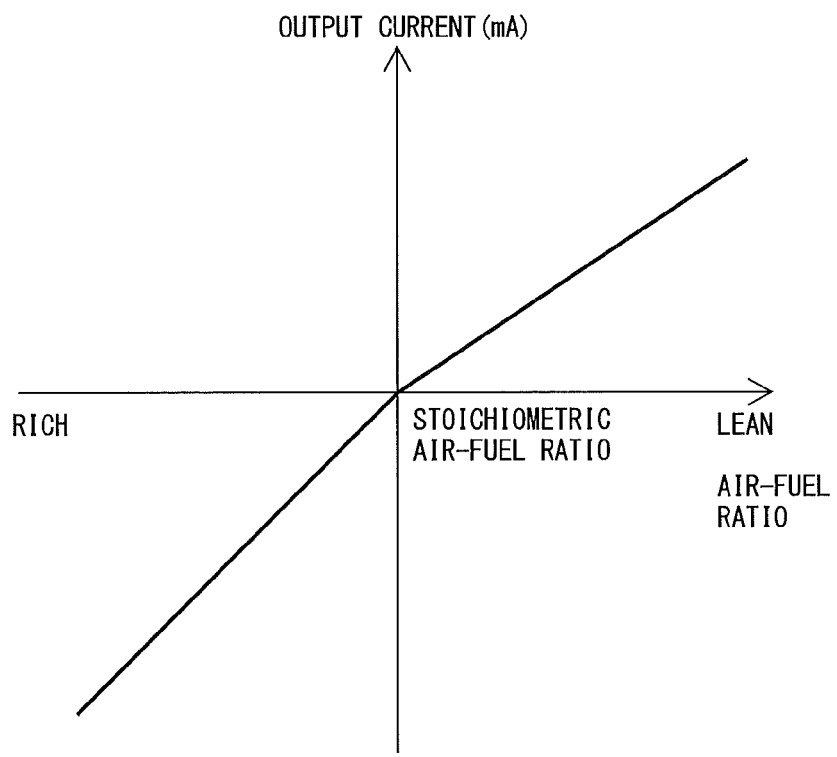
FIG. 5 shows the relationship between the exhaust air-fuel ratio around the air-fuel ratio sensor and the output current thereof.

The thus configured air-fuel ratio sensors 40 and 41 have the output characteristics which are shown in FIG. 5. That is, in the air-fuel ratio sensors 40 and 41, the larger the exhaust air-fuel ratio (that is, the leaner), the larger output currents Ir of the air-fuel ratio sensor 40 and 41 become. In addition, the air-fuel ratio sensors 40 and 41 are configured so that the output currents Ir become zero when the exhaust air-fuel ratio is the stoichiometric air-fuel ratio.

<Circuits of Voltage Application Device and Current Detection Device>

Figure 6:
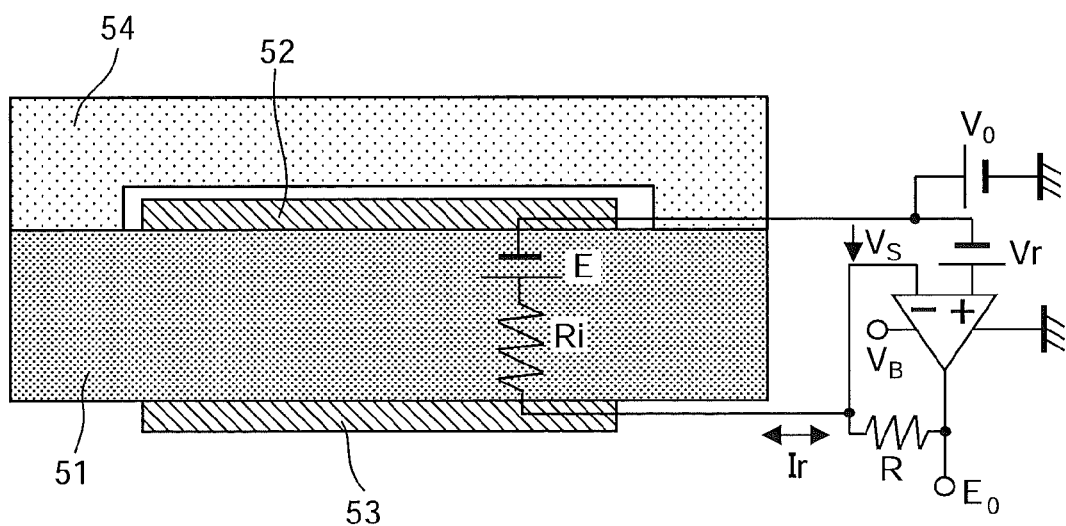
FIG. 6 is a view which shows an example of a specific circuit which forms a voltage application device and current detection device.

FIG. 6 shows an example of the specific circuits which form the voltage application device 60 and current detection device 61. In the illustrated example, the electromotive force E which occurs due to the oxygen cell characteristic is expressed as "E", the internal resistance of the solid electrolyte layer 51 is expressed as "Ri", and the difference of electrical potential across the two electrodes 52, 53 is expressed as "Vs".

As will be understood from FIG. 6, the voltage application device 60 basically performs negative feedback control so that the electromotive force E which occurs due to the oxygen cell characteristic matches the sensor applied voltage Vr. In other words, the voltage application device 60 performs negative feedback control so that even when a change in the oxygen concentration ratio between the two lateral surfaces of the solid electrode layer 51 causes the potential difference Vs between the two electrodes 52 and 53 to change, this potential difference Vs becomes the sensor applied voltage Vr.

Therefore, when the exhaust air-fuel ratio becomes the stoichiometric air-fuel ratio and no change occurs in the oxygen concentration ratio between the two lateral surfaces of the solid electrolyte layer 51, the oxygen concentration ratio between the two lateral surfaces of the solid electrolyte layer 51 becomes the oxygen concentration ratio corresponding to the sensor applied voltage Vr. In this case, the electromotive force E conforms to the sensor applied voltage Vr, the potential difference Vs between the two electrodes 52 and 53 also becomes the sensor applied voltage Vr, and, as a result, the current Ir does not flow.

On the other hand, when the exhaust air-fuel ratio becomes an air-fuel ratio which is different from the stoichiometric air-fuel ratio and a change occurs in the oxygen concentration ratio between the two lateral surfaces of the solid electrolyte layer 51, the oxygen concentration ratio between the two lateral surfaces of the solid electrolyte layer 51 does not become an oxygen concentration ratio corresponding to the sensor applied voltage Vr. In this case, the electromotive force E becomes a value different from the sensor applied voltage Vr. Therefore, due to negative feedback control, a potential difference Vs is applied between the two electrodes 52 and 53 so that oxygen ions move between the two lateral surfaces of the solid electrolyte layer 51 so that the electromotive force E conforms to the sensor applied voltage Vr. Further, current Ir flows along with movement of oxygen ions at this time. As a result, the electromotive force E converges to the sensor applied voltage Vr. If the electromotive force E converges to the sensor applied voltage Vr, finally the potential difference Vs also converges to the sensor applied voltage Vr.

Therefore, the voltage application device 60 can be said to substantially apply the sensor applied voltage Vr between the two electrodes 52 and 53. Note that, the electrical circuit of the voltage application device 60 does not have to be one such as shown in FIG. 6. The circuit may be any form of device so long as able to substantially apply the sensor applied voltage Vr across the two electrodes 52, 53.

Further, the current detection device 61 does not actually detect the current. It detects the voltage $E_0$ to calculate the current from this voltage $E_0$. In this regard, $E_0$ is expressed as in the following equation (1).

$$E_0 = Vr + V_0 + I_r R \quad (1)$$

wherein, $V_0$ is the offset voltage (voltage applied so that $E_0$ does not become a negative value, for example, 3V), while R is the value of the resistance shown in FIG. 6.

In equation (1), the sensor applied voltage Vr, offset voltage $V_0$, and resistance value R are constant, and therefore the voltage $E_0$ changes in accordance with the current Ir. For this reason, if detecting the voltage $E_0$, it is possible to calculate the current Ir from that voltage $E_0$.

Therefore, the current detection device 61 can be said to substantially detect the current Ir which flows across the two electrodes 52, 53. Note that, the electrical circuit of the current detection device 61 does not have to be one such as shown in FIG. 6. If possible to detect the current Ir flowing across the two electrodes 52, 53, any form of device may be used.

<Summary of Control of Air-Fuel Ratio>

Next, a summary of the air-fuel ratio control in a control system of an internal combustion engine of the present invention will be explained. In the present embodiment, based on the output current Irup of the upstream side air-fuel ratio sensor 40, feedback control is performed so that the output current (that is, the air-fuel ratio of the exhaust gas flowing into the exhaust purification catalyst) Irup of the upstream side air-fuel ratio sensor 40 becomes a value corresponding to the target air-fuel ratio.

The target air-fuel ratio is set based on the output current of the downstream side air-fuel ratio sensor 41. Specifically, the target air-fuel ratio is set to the lean set air-fuel ratio when the output current Irdwn of the downstream side air-fuel ratio sensor 41 becomes a rich judged reference value Iref or less and is maintained at that air-fuel ratio. In this regard, the rich judged reference value Iref is a value corresponding to a predetermined rich judged air-fuel ratio (for example, 14.55), which is slightly richer than the stoichiometric air-fuel ratio. Further, the lean set air-fuel ratio is a predetermined air-fuel ratio leaner than the stoichiometric air-fuel ratio by a certain extent. For example, it is 14.65 to 20, preferably 14.68 to 18, more preferably 14.7 to 16 or so.

If the target air-fuel ratio is changed to the lean set air-fuel ratio, the oxygen storage amount OSAsc of the upstream side exhaust purification catalyst 20 is estimated. The oxygen storage amount OSAsc is estimated based on the output current Irup of the upstream side air-fuel ratio sensor 40, and the estimated value of the amount of intake air to the combustion chamber 5, which is calculated based on the air flow meter 39, etc., or the amount of fuel injection from the fuel injector 11, etc. Further, if the estimated value of the oxygen storage amount OSAsc becomes a predetermined judged reference storage amount Cref or more, the target air-fuel ratio which was the lean set air-fuel ratio up to then is changed to a slight rich set air-fuel ratio and is maintained at that air-fuel ratio. The slight rich set air-fuel ratio is a predetermined air-fuel ratio slightly richer than the stoichiometric air-fuel ratio. For example, it is 13.5 to 14.58, preferably 14 to 14.57, more preferably 14.3 to 14.55 or so. After that, when the output current Irdwn of the downstream side air-fuel ratio sensor 41 again becomes the rich judged reference value Iref or less, the target air-fuel ratio is again set to the lean set air-fuel ratio, and then a similar operation is repeated.

In this way, in the present embodiment, the target air-fuel ratio of the exhaust gas flowing into the upstream side exhaust purification catalyst 20 is alternately set to the lean set air-fuel ratio and the slight rich set air-fuel ratio. In particular, in the present embodiment, the difference between the lean set air-fuel ratio and the stoichiometric air-fuel ratio is larger than the difference between the slight rich set air-fuel ratio and the stoichiometric air-fuel ratio. Therefore, in the present embodiment, the target air-fuel ratio is alternately set to lean set air-fuel ratio for a short period of time and slight rich set air-fuel ratio for a long period of time.

<Explanation of Control Using Time Chart>

Figure 7:
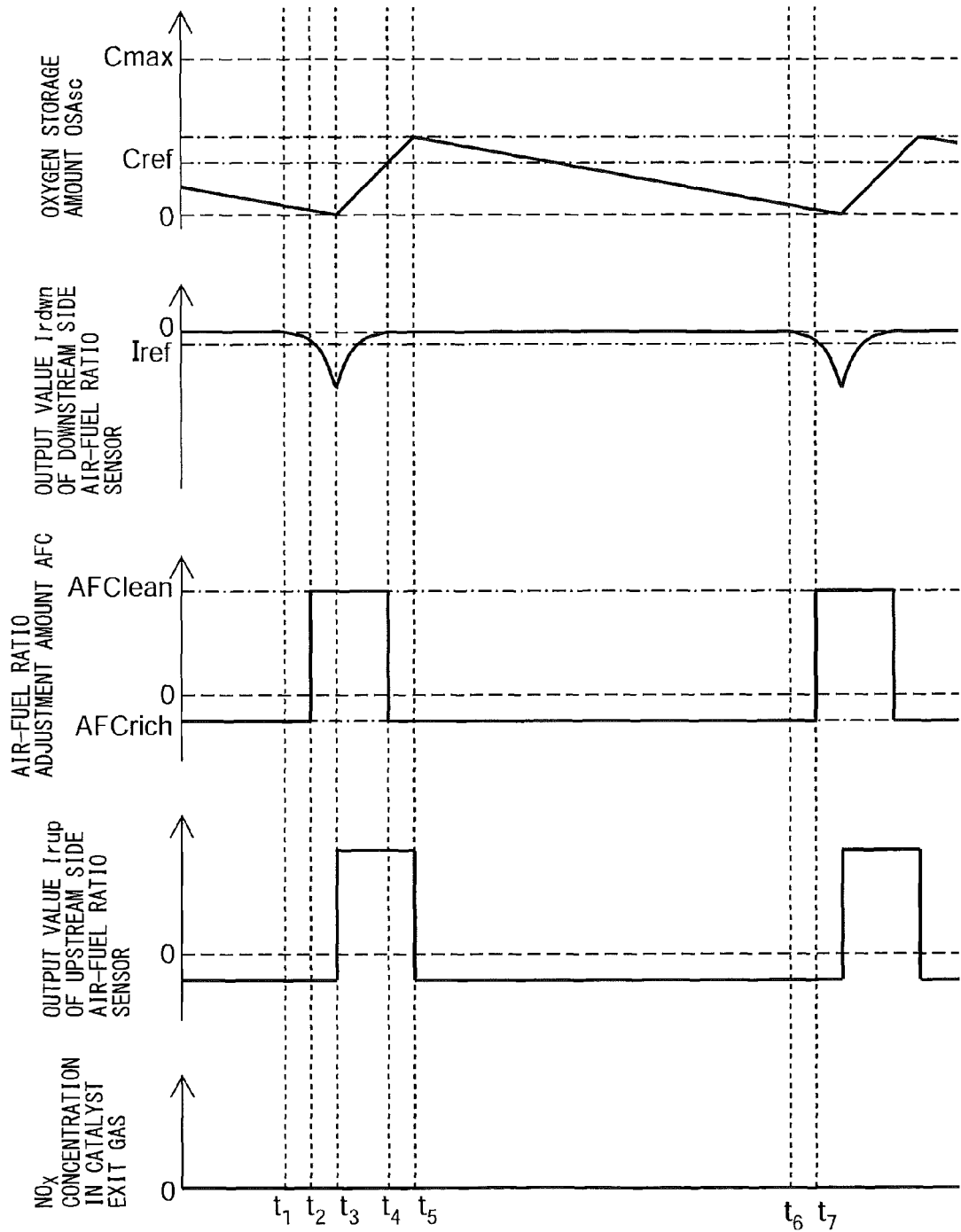
FIG. 7 is a time chart of the oxygen storage amount of the exhaust purification catalyst, etc.

Referring to FIG. 7, the above-mentioned such operation will be explained in detail. FIG. 7 is a time chart of the oxygen storage amount OSAsc of the upstream side exhaust purification catalyst 20, the output current Irdwn of the downstream side air-fuel ratio sensor 41, the output current Irup of the upstream side air-fuel ratio sensor 40 and NOx concentration in the exhaust gas flowing out from the upstream side exhaust purification catalyst 20, in the case of performing air-fuel ratio control in a control system of an internal combustion engine of the present invention.

Note that, the output current Irup of the upstream side air-fuel ratio sensor 40 becomes zero when the air-fuel ratio of the exhaust gas flowing into the upstream side exhaust purification catalyst 20 is the stoichiometric air-fuel ratio, becomes a negative value when the air-fuel ratio of the exhaust gas is a rich air-fuel ratio, and becomes a positive value when the air-fuel ratio of the exhaust gas is a lean air-fuel ratio. Further, when the air-fuel ratio of the exhaust gas flowing into the upstream side exhaust purification catalyst 20 is a rich air-fuel ratio or lean air-fuel ratio, the greater the difference from the stoichiometric air-fuel ratio, the larger the absolute value of the output current Irup of the upstream side air-fuel ratio sensor 40. The output current Irdwn of the downstream side air-fuel ratio sensor 41 also changes in accordance with the air-fuel ratio of the exhaust gas flowing out from the upstream side exhaust purification catalyst 20, similarly to the output current Irup of the upstream side air-fuel ratio sensor 40. Further, the air-fuel ratio adjustment amount AFC is a adjustment amount relating to the target air-fuel ratio of the exhaust gas flowing into the upstream side exhaust purification catalyst 20. When the air-fuel ratio adjustment amount AFC is 0, the target air-fuel ratio is the stoichiometric air-fuel ratio, when the air-fuel ratio adjustment amount AFC is a positive value, the target air-fuel ratio becomes a lean air-fuel ratio, and when the air-fuel ratio adjustment amount AFC is a negative value, the target air-fuel ratio becomes a rich air-fuel ratio.

In the illustrated example, in the state before the time $t_1$, the air-fuel ratio adjustment amount AFC is set to the slight rich set adjustment amount AFCrich. The slight rich set adjustment amount AFCrich is a value corresponding to the slight rich set air-fuel ratio and a value smaller than 0. Therefore, the target air-fuel ratio is set to a rich air-fuel ratio. Along with this, the output current Irup of the upstream side air-fuel ratio sensor 40 becomes a negative value. The exhaust gas flowing into the upstream side exhaust purification catalyst 20 contains unburned gas, and therefore the oxygen storage amount OSAsc of the upstream side exhaust purification catalyst 20 gradually decreases. However, the unburned gas contained in the exhaust gas is purified at the upstream side exhaust purification catalyst 20, and therefore the output current Irdwn of the downstream side air-fuel ratio sensor is substantially zero (corresponding to the stoichiometric air-fuel ratio). At this time, the air-fuel ratio of the exhaust gas flowing into the upstream side exhaust purification catalyst 20 becomes a rich air-fuel ratio, and therefore the amount of $NO_x$ exhausted from the upstream side exhaust purification catalyst 20 is suppressed.

If the oxygen storage amount OSAsc of the upstream side exhaust purification catalyst 20 gradually decreases, the oxygen storage amount OSAsc decreases to less than the lower limit storage amount (see Clowlim of FIG. 2) at the time $t_1$. If the oxygen storage amount OSAsc decreases to less than the lower limit storage amount, part of the unburned gas flowing into the upstream side exhaust purification catalyst 20 flows out without being purified at the upstream side exhaust purification catalyst 20. For this reason, after the time $t_1$, the output current Irdwn of the downstream side air-fuel ratio sensor 41 gradually falls along with the decrease in the oxygen storage amount OSAsc of the upstream side exhaust purification catalyst 20. At this time as well, the air-fuel ratio of the exhaust gas flowing into the upstream side exhaust purification catalyst 20 becomes a rich air-fuel ratio, and therefore the amount of $NO_x$ exhausted from the upstream side exhaust purification catalyst 20 is suppressed.

Then, at the time $t_2$, the output current Irdwn of the downstream side air-fuel ratio sensor 41 reaches the rich judged reference value Iref corresponding to the rich judged air-fuel ratio. In the present embodiment, if the output current Irdwn of the downstream side air-fuel ratio sensor 41 reaches the rich judged reference value Iref, the air-fuel ratio adjustment amount AFC is switched to the lean set adjustment amount AFClean so as to suppress the decrease of the oxygen storage amount OSAsc of the upstream side exhaust purification catalyst 20. The lean set adjustment amount AFClean is a value corresponding to the lean set air-fuel ratio and is a value larger than 0. Therefore, the target air-fuel ratio is set to a lean air-fuel ratio.

Note that, in the present embodiment, the air-fuel ratio adjustment amount AFC is switched after the output current Irdwn of the downstream side air-fuel ratio sensor 41 reaches the rich judged reference value Iref, that is, after the air-fuel ratio of the exhaust gas flowing out from the upstream side exhaust purification catalyst 20 reaches the rich judged air-fuel ratio. This is because even if the oxygen storage amount of the upstream side exhaust purification catalyst 20 is sufficient, the air-fuel ratio of the exhaust gas flowing out from the upstream side exhaust purification catalyst 20 sometimes deviates slightly from the stoichiometric air-fuel ratio. That is, if it is judged that the oxygen storage amount has decreased to less than the lower limit storage amount when the output current Irdwn deviates slightly from zero (corresponding to the stoichiometric air-fuel ratio), even if there is actually a sufficient oxygen storage amount, there is a possibility that it is judged that the oxygen storage amount decreases to lower than the lower limit storage amount. Therefore, in the present embodiment, it is judged the oxygen storage amount decreases lower than the lower limit storage amount, only when the air-fuel ratio of the exhaust gas flowing out from the upstream side exhaust purification catalyst 20 reaches the rich judged air-fuel ratio. Conversely speaking, the rich judged air-fuel ratio is set to an air-fuel ratio which the air-fuel ratio of the exhaust gas flowing out from the upstream side exhaust purification catalyst 20 does not reach at all when the oxygen storage amount of the upstream side exhaust purification catalyst 20 is sufficient.

Even if, at the time $t_2$, the target air-fuel ratio is switched to the lean air-fuel ratio, the air-fuel ratio of the exhaust gas flowing into the upstream side exhaust purification catalyst 20 does not immediately become the lean air-fuel ratio, and a certain extent of delay arises. As a result, the air-fuel ratio of the exhaust gas flowing into the upstream side exhaust purification catalyst 20 changes from the rich air-fuel ratio to the lean air-fuel ratio at the time $t_3$. Note that, during the times $t_2$ to $t_3$, the air-fuel ratio of the exhaust gas flowing out from the upstream side exhaust purification catalyst 20 is a rich air-fuel ratio, and therefore this exhaust gas contains unburned gas. However, the amount of discharge of $NO_x$ from the upstream side exhaust purification catalyst 20 is suppressed.

At the time $t_3$, if the air-fuel ratio of the exhaust gas flowing into the upstream side exhaust purification catalyst 20 changes to the lean air-fuel ratio, the oxygen storage amount OSAsc of the upstream side exhaust purification catalyst 20 increases. Further, along with this, the air-fuel ratio of the exhaust gas flowing out from the upstream side exhaust purification catalyst 20 changes to the stoichiometric air-fuel ratio, and the output current Irdwn of the downstream side air-fuel ratio sensor 41 also converges to zero. Although the air-fuel ratio of the exhaust gas flowing into the upstream side exhaust purification catalyst 20 is a lean air-fuel ratio at this time, the upstream side exhaust purification catalyst 20 has sufficient leeway in the oxygen storage ability, and therefore the oxygen in the inflowing exhaust gas is stored in the upstream side exhaust purification catalyst 20 and the $NO_x$ is reduced and purified. For this reason, the amount of $NO_x$ exhausted from the upstream side exhaust purification catalyst 20 is suppressed.

Then, if the oxygen storage amount OSAsc of the upstream side exhaust purification catalyst 20 increases, at the time $t_4$, the oxygen storage amount OSAsc reaches the judged reference storage amount Cref. In the present embodiment, if the oxygen storage amount OSAsc becomes the judged reference storage amount Cref, the air-fuel ratio adjustment amount AFC is switched to a slight rich set adjustment amount AFCrich (value smaller than 0) to stop the storage of oxygen in the upstream side exhaust purification catalyst 20. Therefore, the target air-fuel ratio is set to the rich air-fuel ratio.

However, as explained above, a delay occurs from when the target air-fuel ratio is switched to when the air-fuel ratio of the exhaust gas flowing into the upstream side exhaust purification catalyst 20 actually changes. For this reason, even if switching at the time $t_4$, after a certain extent of time passes from it, at the time $t_5$, the air-fuel ratio of the exhaust gas flowing into the upstream side exhaust purification catalyst 20 changes from the lean air-fuel ratio to the rich air-fuel ratio. During the times t4 to t5, the air-fuel ratio of the exhaust gas flowing into the upstream side exhaust purification catalyst 20 is the lean air-fuel ratio, and therefore the oxygen storage amount OSAsc of the upstream side exhaust purification catalyst 20 increases.

However, the judged reference storage amount Cref is set sufficiently lower than the maximum oxygen storage amount Cmax or the upper limit storage amount (see Cuplim in FIG. 2), and therefore even at the time $t_5$, the oxygen storage amount OSAsc does not reach the maximum oxygen storage amount Cmax or the upper limit storage amount. Conversely speaking, the judged reference storage amount Cref is set to an amount sufficiently small so that the oxygen storage amount OSAsc does not reach the maximum oxygen storage amount Cmax or the upper limit storage amount even if a delay occurs from when switching the target air-fuel ratio to when the air-fuel ratio of the exhaust gas flowing into the upstream side exhaust purification catalyst 20 actually changes. For example, the judged reference storage amount Cref is set to ¾ or less of the maximum oxygen storage amount Cmax, preferably ½ or less, more preferably ⅕ or less. Therefore, during times $t_4$ to $t_5$ as well, the amount of $NO_x$ exhausted from the upstream side exhaust purification catalyst 20 is suppressed.

After the time $t_5$, the air-fuel ratio adjustment amount AFC is set to the slight rich set adjustment amount AFCrich. Therefore, the target air-fuel ratio is set to the rich air-fuel ratio. Along with this, the output current Irup of the upstream side air-fuel ratio sensor 40 becomes a negative value. The exhaust gas flowing into the upstream side exhaust purification catalyst 20 contains unburned gas, and therefore the oxygen storage amount OSAsc of the upstream side exhaust purification catalyst 20 gradually decreases. At the time $t_6$, in the same way as the time $t_1$, the oxygen storage amount OSAsc decreases below the lower limit storage amount. At this time as well, the air-fuel ratio of the exhaust gas flowing into the upstream side exhaust purification catalyst 20 becomes a rich air-fuel ratio, and therefore the amount of $NO_x$ exhausted from the upstream side exhaust purification catalyst 20 is suppressed.

Next, at the time $t_7$, in the same way as the time $t_2$, the output current Irdwn of the downstream side air-fuel ratio sensor 41 reaches the rich judged reference value Iref corresponding to the rich judged air-fuel ratio. Due to this, the air-fuel ratio adjustment amount AFC is switched to the value AFClean corresponding to the lean set air-fuel ratio. Then, the cycle of the above-mentioned times $t_1$ to $t_6$ is repeated. Note that, during these cycles, the applied voltage Vrdwn to the downstream side air-fuel ratio sensor 41 is maintained at a voltage whereby the exhaust air-fuel ratio at the time of zero current becomes the rich judged air-fuel ratio.

Note that, such control of the air-fuel ratio adjustment amount AFC is performed by the ECU 31. Therefore, the ECU 31 can be said to comprise: an oxygen storage amount increasing means for continuously setting a target air-fuel ratio of exhaust gas flowing into the upstream side catalyst 20 to a lean set air-fuel ratio when the air-fuel ratio of the exhaust gas which was detected by the downstream side air-fuel ratio sensor 41 becomes a rich judged air-fuel ratio or less, until the oxygen storage amount OSAsc of the upstream side catalyst 20 becomes the judged reference storage amount Cref; and an oxygen storage amount decreasing means for continuously setting the target air-fuel ratio to a weak rich set air-fuel ratio when the oxygen storage amount OSAsc of the upstream side catalyst 20 becomes the judged reference storage amount Cref or more so that the oxygen storage amount OSAsc never reaches the maximum oxygen storage amount Cmaxn but decreases toward zero.

As will be understood from the above explanation, according to the above embodiment, it is possible to constantly suppress the amount of discharge of $NO_x$ from the upstream side exhaust purification catalyst 20. That is, so long as performing the above-mentioned control, basically the amount of discharge of $NO_x$ from the upstream side exhaust purification catalyst 20 is small.

Further, in general, if the oxygen storage amount OSAsc is estimated based on the output current Irup of the upstream side air-fuel ratio sensor 40 and the estimated value of the intake air amount, etc., there is the possibility that error will occur. In the present embodiment as well, the oxygen storage amount OSAsc is estimated over the times $t_3$ to $t_4$, and therefore the estimated value of the oxygen storage amount OSAsc includes some error. However, even if such error is included, if setting the judged reference storage amount Cref to sufficiently lower than the maximum oxygen storage amount Cmax or upper limit storage amount, the actual oxygen storage amount OSAsc will almost never reach the maximum oxygen storage amount Cmax or upper limit storage amount. Therefore, from such a viewpoint as well, it is possible to suppress the amount of discharge of $NO_x$ from the upstream side exhaust purification catalyst 20.

Further, if the oxygen storage amount of the exhaust purification catalyst is maintained constant, the oxygen storage ability of the exhaust purification catalyst will fall. As opposed to this, according to the present embodiment, the oxygen storage amount OSAsc constantly fluctuates up and down, so the oxygen storage ability is kept from falling.

Note that, in the above embodiment, during the times $t_2$ to $t_4$, the air-fuel ratio adjustment amount AFC is maintained at the lean set adjustment amount AFClean. However, in such a time period, the air-fuel ratio adjustment amount AFC does not necessarily have to be maintained constant. It may be set to gradually decrease or otherwise change. Similarly, during the times $t_4$ to $t_7$, the air-fuel ratio adjustment amount AFC is maintained at the slight rich set adjustment amount AFCrich. However, in such a time period, the air-fuel ratio adjustment amount AFC does not necessarily have to be maintained constant. It may be set to gradually decrease or otherwise change.

However, even in this case, the air-fuel ratio adjustment amount AFC during the times $t_2$ to $t_4$ is set so that the difference of the average value of the target air-fuel ratio and the stoichiometric air-fuel ratio in that period becomes larger than the difference between the average value of the target air-fuel ratio and the stoichiometric air-fuel ratio during the times $t_4$ to $t_7$.

Further, in the above embodiment, the oxygen storage amount OSAsc of the upstream side exhaust purification catalyst 20 is estimated, based on the output current Irup of the upstream side air-fuel ratio sensor 40 and the estimated value of the amount of intake air to the combustion chamber 5, etc. However, the oxygen storage amount OSAsc may also be calculated by other parameters in addition to these parameters and may be estimated based on parameters which are different from these parameters. Further, in the above embodiment, if the estimated value of the oxygen storage amount OSAsc becomes the judged reference storage amount Cref or more, the target air-fuel ratio is switched from the lean set air-fuel ratio to the slight rich set air-fuel ratio. However, the timing of switching the target air-fuel ratio from the lean set air-fuel ratio to the slight rich set air-fuel ratio may, for example, use as a reference another parameter, such as the engine operating time etc. from when switching the target air-fuel ratio from the slight rich set air-fuel ratio to the lean set air-fuel ratio. However, even in this case, the target air-fuel ratio has to be switched from the lean set air-fuel ratio to the slight rich set air-fuel ratio in the period when the oxygen storage amount OSAsc of the upstream side exhaust purification catalyst 20 is estimated to be smaller than the maximum oxygen storage amount.

<Explanation of Control Using Also Downstream Side Catalyst>

Further, in the present embodiment, in addition to the upstream side exhaust purification catalyst 20, a downstream side exhaust purification catalyst 24 is provided. The oxygen storage amount OSAufc of the downstream side exhaust purification catalyst 24 becomes a value near the maximum storage amount Cmax by fuel cut control which is performed every certain extent of time period. For this reason, even if exhaust gas containing unburned gas flows out from the upstream side exhaust purification catalyst 20, the unburned gas is oxidized and purified at the downstream side exhaust purification catalyst 24.

Note that, "fuel cut control" is control to prevent injection of fuel from the fuel injectors 11 even if the crankshaft or pistons 3 are in an operating state, at the time of deceleration, etc., of the vehicle which mounts the internal combustion engine. If performing this control, a large amount of air flows into the two catalysts 20, 24.

Figure 8:
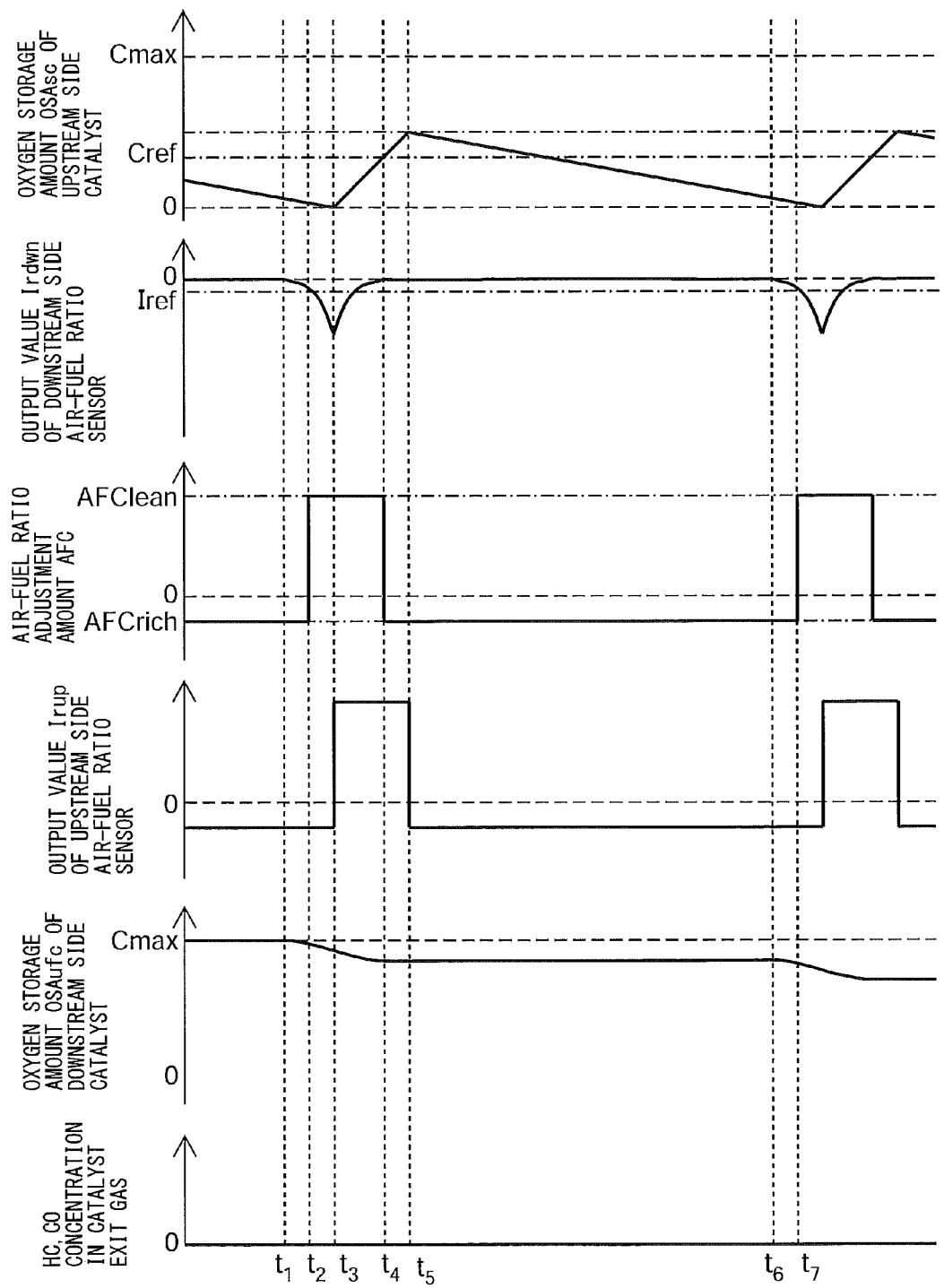
FIG. 8 is a time chart of the oxygen storage amount of the exhaust purification catalyst, etc.

Below, referring to FIG. 8, the trend in the oxygen storage amount OSAufc at the downstream side exhaust purification catalyst 24 will be explained. FIG. 8 is a view similar to FIG. 7 and shows, instead of the trend in the concentration of $NO_x$ of FIG. 7, the trends in the oxygen storage amount OSAufc of the downstream side exhaust purification catalyst 24 and the concentration of unburned gas (HC, CO, etc.) in the exhaust gas flowing out from the downstream side exhaust purification catalyst 24. Further, in the example shown in FIG. 8, control the same as the example shown in FIG. 7 is performed.

In the example shown in FIG. 8, fuel cut control is performed before the time $t_1$. For this reason, before the time $t_1$, the oxygen storage amount OSAufc of the downstream side exhaust purification catalyst 24 is a value close to the maximum oxygen storage amount Cmax. Further, before the time $t_1$, the air-fuel ratio of the exhaust gas flowing out from the upstream side exhaust purification catalyst 20 is held at substantially the stoichiometric air-fuel ratio. For this reason, the oxygen storage amount OSAufc of the downstream side exhaust purification catalyst 24 is maintained constant.

After that, during the times $t_1$ to $t_4$, the air-fuel ratio of the exhaust gas flowing out from the upstream side exhaust purification catalyst 20 becomes the rich air-fuel ratio. For this reason, exhaust gas containing unburned gas flows into the downstream side exhaust purification catalyst 24.

As explained above, since the downstream side exhaust purification catalyst 24 stores a large amount of oxygen, if the exhaust gas flowing into the downstream side exhaust purification catalyst 24 contains unburned gas, the unburned gas is oxidized and purified by the stored oxygen. Further, along with this, the oxygen storage amount OSAufc of the downstream side exhaust purification catalyst 24 decreases. However, during the times $t_1$ to $t_4$, the unburned gas flowing out from the upstream side exhaust purification catalyst 20 is not that large, and therefore the amount of decrease of the oxygen storage amount OSAufc in this interval is slight. Therefore, the unburned gas flowing out from the upstream side exhaust purification catalyst 20 during the times $t_1$ to $t_4$ is completely oxidized and purified at the downstream side exhaust purification catalyst 24.

After the time $t_6$ as well, every certain extent of time interval, in the same way as the case during the times $t_1$ to $t_4$, unburned gas flows out from the upstream side exhaust purification catalyst 20. The thus flowing out unburned gas is basically oxidized and purified by the oxygen which is stored in the downstream side exhaust purification catalyst 24. Therefore, unburned gas almost never flows out from the downstream side exhaust purification catalyst 24. As explained above, considering that $NO_x$ discharge amount from the upstream side exhaust purification catalyst 20 is kept small, according to the present embodiment, the amounts of discharge of unburned gas and $NO_x$ from the downstream side exhaust purification catalyst 24 are always made small.

<Explanation of Specific Control>

Figure 9:
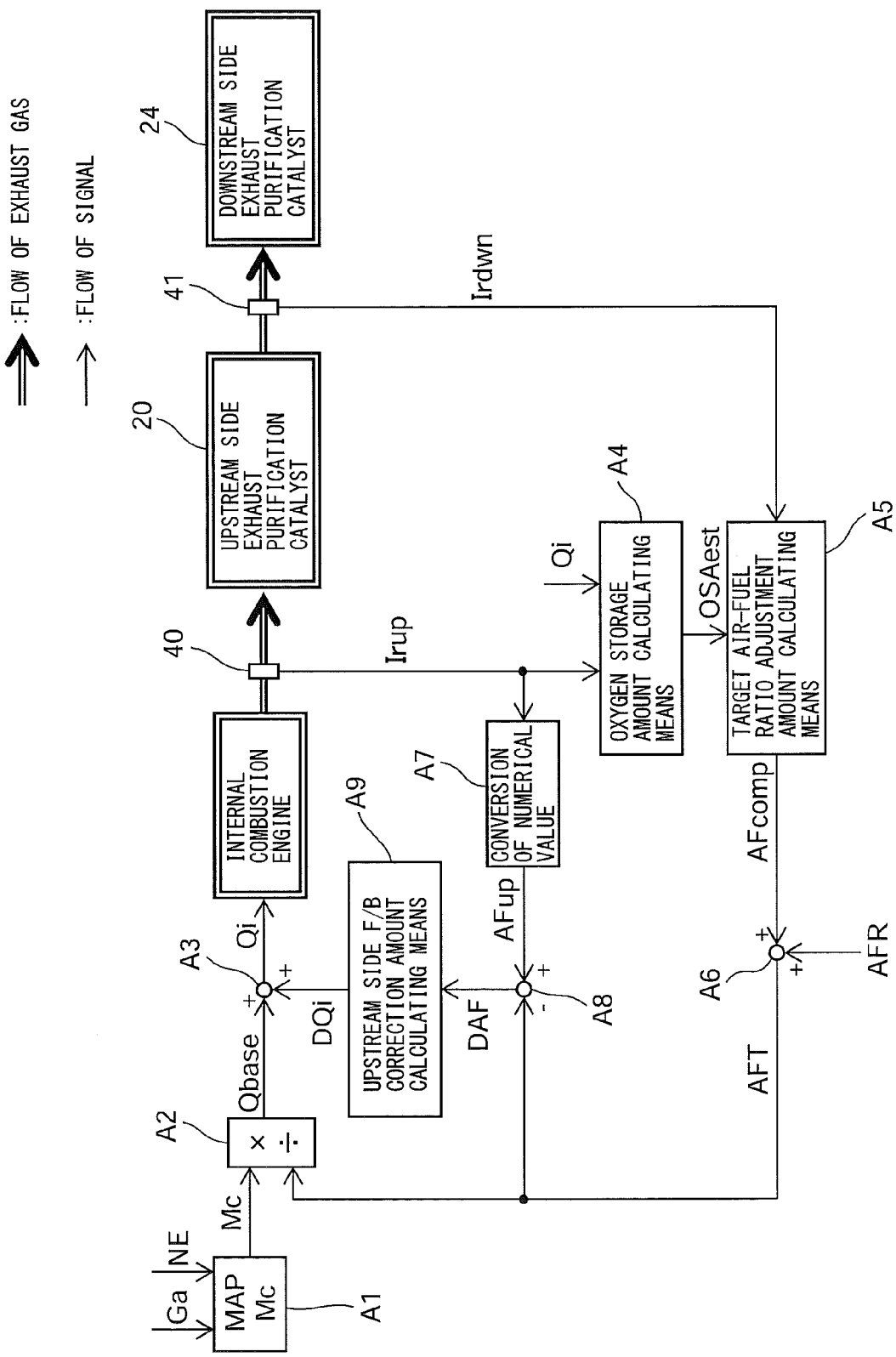
FIG. 9 is a functional block diagram of a control system.
Figure 10:
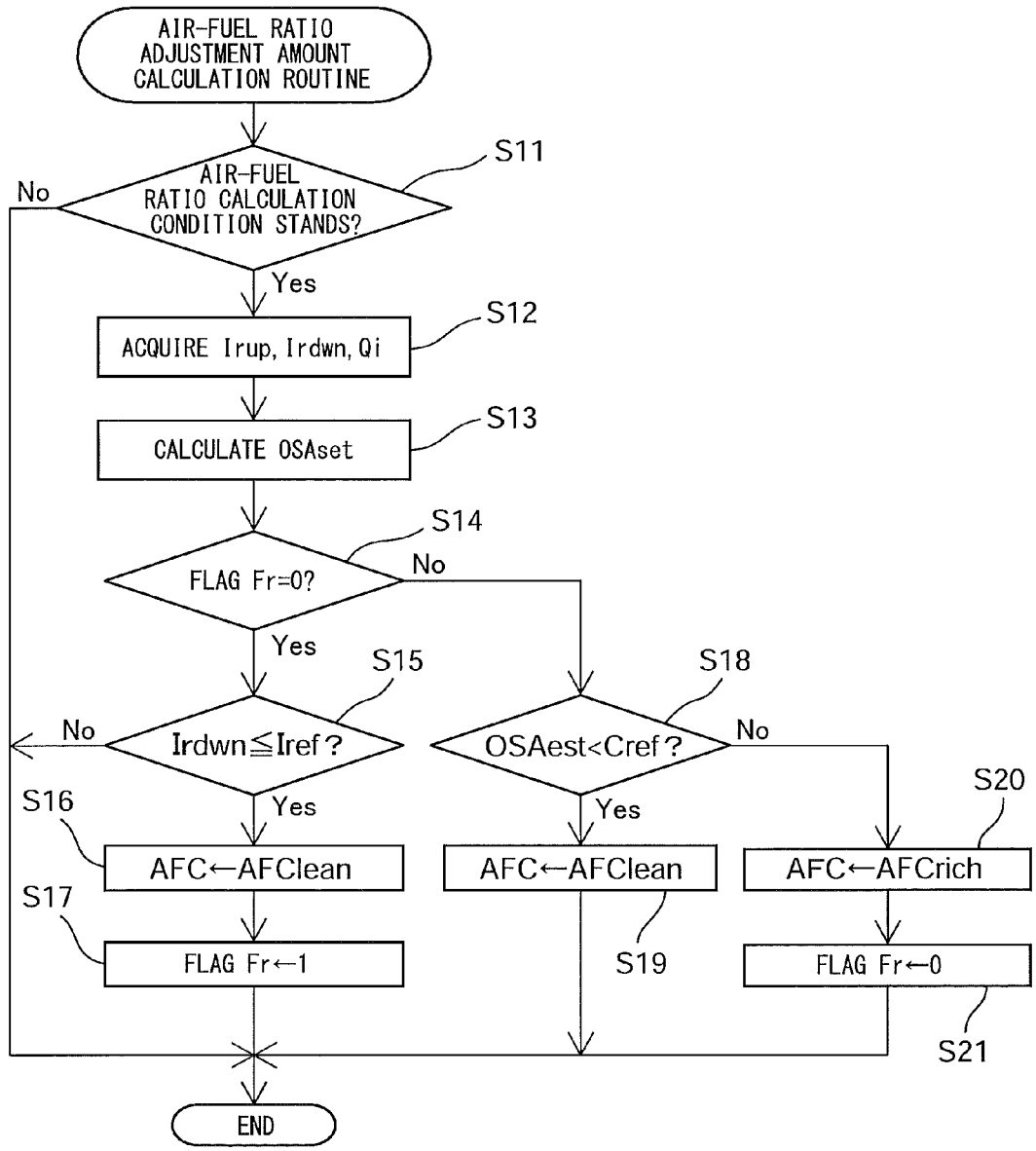
FIG. 10 is a flow chart which shows a control routine of control for calculation of an air-fuel ratio adjustment amount.

Next, referring to FIGS. 9 and 10, a control system in the above embodiment will be specifically explained. The control system in the present embodiment, as shown by the functional block diagram of FIG. 9, is configured including the functional blocks A1 to A9. Below, each functional block will be explained while referring to FIG. 9.

<Calculation of Fuel Injection>

First, calculation of the fuel injection will be explained. In calculating the fuel injection, the cylinder intake air calculating means A1, basic fuel injection calculating means A2, and fuel injection calculating means A3 are used.

The cylinder intake air calculating means A1 calculates the intake air amount Mc to each cylinder based on the intake air flow rate Ga measured by the air flow meter 39, the engine speed NE calculated based on the output of the crank angle sensor 44, and the map or calculation formula stored in the ROM 34 of the ECU 31.

The basic fuel injection calculating means A2 divides the cylinder intake air amount Mc, which is calculated by the cylinder intake air calculating means A1, by the target air-fuel ratio AFT which is calculated by the later explained target air-fuel ratio setting means A6 to thereby calculate the basic fuel injection amount Qbase (Qbase=Mc/AFT).

The fuel injection calculating means A3 adds the basic fuel injection amount Qbase calculated by the basic fuel injection calculating means A2 and the later explained F/B correction amount DQi, to calculate the fuel injection amount Qi (Qi=Qbase+DQi). The fuel injector 11 is commanded to inject fuel so that the fuel of the fuel injection amount Qi which was calculated in this way is injected.

<Calculation of Target Air-Fuel Ratio>

Next, calculation of the target air-fuel ratio will be explained. In calculation of the target air-fuel ratio, an oxygen storage amount calculating means A4, target air-fuel ratio adjustment amount calculating means A5, and target air-fuel ratio setting means A6 are used.

The oxygen storage amount calculating means A4 calculates the estimated value OSAest of the oxygen storage amount of the upstream side exhaust purification catalyst 20, based on the fuel injection amount Qi calculated by the fuel injection calculating means A3 and the output current Irup of the upstream side air-fuel ratio sensor 40. For example, the oxygen storage amount calculating means A4 multiplies the difference between the air-fuel ratio corresponding to the output current Irup of the upstream side air-fuel ratio sensor 40 and the stoichiometric air-fuel ratio, with the fuel injection amount Qi, and cumulatively adds the calculated values to calculate the estimated value OSAest of the oxygen storage amount. Note that, the oxygen storage amount calculating means A4 need not constantly estimate the oxygen storage amount of the upstream side exhaust purification catalyst 20. For example, it is possible to estimate the oxygen storage amount only for the period from when the target air-fuel ratio is actually switched from the rich air-fuel ratio to the lean air-fuel ratio (time $t_3$ in FIG. 7) to when the estimated value OSAest of the oxygen storage amount reaches the judged reference storage amount Cref (time $t_4$ in FIG. 7).

In the target air-fuel ratio adjustment amount calculating means A5, the air-fuel ratio adjustment amount AFC of the target air-fuel ratio is calculated, based on the estimated value OSAest of the oxygen storage amount calculated by the oxygen storage amount calculating means A4 and the output current Irdwn of the downstream side air-fuel ratio sensor 41. Specifically, the air-fuel ratio adjustment amount AFC is set to the lean set adjustment amount AFClean when the output current Irdwn of the downstream side air-fuel ratio sensor 41 becomes the rich judged reference value Iref (value corresponding to the rich judged air-fuel ratio) or less. Then, the air-fuel ratio adjustment amount AFC is maintained at the lean set adjustment amount AFClean until the estimated value OSAest of the oxygen storage amount reaches the judged reference storage amount Cref. If the estimated value OSAest of the oxygen storage amount reaches the judged reference storage amount Cref, the air-fuel ratio adjustment amount AFC is set to the slight rich set adjustment amount AFCrich. After that, the air-fuel ratio adjustment amount AFC is maintained at a slight rich set adjustment amount AFCrich until the output current Irdwn of the downstream side air-fuel ratio sensor 41 becomes the rich judged reference value (value corresponding to the rich judged air-fuel ratio) or less.

The target air-fuel ratio setting means A6 adds the reference air-fuel ratio, which is, in the present embodiment, the stoichiometric air-fuel ratio AFR, and the air-fuel ratio adjustment amount AFC calculated by the target air-fuel ratio adjustment amount calculating means AS to thereby calculate the target air-fuel ratio AFT. Therefore, the target air-fuel ratio AFT is set to either a slight rich set air-fuel ratio (when the air-fuel ratio adjustment amount AFC is a slight rich set adjustment amount AFCrich) or a lean set air-fuel ratio (when the air-fuel ratio adjustment amount AFC is a lean set adjustment amount AFClean). The thus calculated target air-fuel ratio AFT is input to the basic fuel injection calculating means A2 and the later explained air-fuel ratio difference calculating means A8.

FIG. 10 is a flow chart which shows the control routine for control for calculation of the air-fuel ratio adjustment amount AFC. The illustrated control routine is performed by interruption every certain time interval.

As shown in FIG. 10, first, at step S11, it is judged if the calculating condition of the air-fuel ratio adjustment amount AFC stands. The calculating condition of the air-fuel ratio adjustment amount stands, for example, when a fuel cut control is not performed. If it is judged that the calculating condition of the air-fuel ratio stands at step S 11, the routine proceeds to step S12. At step S12, the output current Irup of the upstream side air-fuel ratio sensor 40, the output current Irdwn of the downstream side air-fuel ratio sensor 41, and the fuel injection amount Qi are acquired. Next, at step S13, the estimated value OSAest of the oxygen storage amount is calculated, based on the output current Irup of the upstream side air-fuel ratio sensor 40 and the fuel injection amount Qi are which were acquired at step S12.

Next, at step S14, it is judged if the lean set flag Fr is set to 0. The lean set flag Fr is set to 1 if the air-fuel ratio adjustment amount AFC is set to the lean set adjustment amount AFClean, and is set to 0 otherwise. If the lean set flag Fr is set to 0 at step S14, the routine proceeds to step S15. At step S15, it is judged if the output current Irdwn of the downstream side air-fuel ratio sensor 41 is the rich judged reference value Iref or less. When it is judged that the output current Irdwn of the downstream side air-fuel ratio sensor 41 is larger than the rich judged reference value Iref, the control routine is ended.

On the other hand, if the oxygen storage amount OSAsc of the upstream side exhaust purification catalyst 20 decreases and the air-fuel ratio of the exhaust gas flowing out from the upstream side exhaust purification catalyst 20 falls, at step S15, it is judged that the output current Irdwn of the downstream side air-fuel ratio sensor 41 is the rich judged reference value Iref or less. In this case, the routine proceeds to step S16 where the air-fuel ratio adjustment amount AFC is set to the lean set adjustment amount AFClean. Next, at step S17, the lean set flag Fr is set to 1 and the control routine is to ended.

In the next control routine, at step S14, it is judged that the lean set flag Fr is not set to 0 and the routine proceeds to step 18. At step S18, it is judged if the estimated value OSAest of the oxygen storage amount which was calculated at step S13 is smaller than the judged reference storage amount Cref. When it is judged that the estimated value OSAest of the oxygen storage amount is smaller than the judged reference storage amount Cref, the routine proceeds to step S19 where the air-fuel ratio adjustment amount AFC continues to be the lean set adjustment amount AFClean. On the other hand, if the oxygen storage amount of the upstream side exhaust purification catalyst 20 increases, finally it is judged at step S18 that the estimated value OSAest of the oxygen storage amount is the judged reference storage amount Cref or more and the routine proceeds to step S20. At step S20, the air-fuel ratio adjustment amount AFC is set to a slight rich set adjustment amount AFCrich, then, at step S21, the lean set flag Fr is reset to 0 and the control routine is ended.

<Calculation of F/B Correction Amount>

Returning again to FIG. 9, calculation of the F/B correction amount based on the output current Irup of the upstream side air-fuel ratio sensor 40 will be explained. In calculation of the F/B correction amount, the numerical value converting means A7, air-fuel ratio difference calculating means A8, and F/B correction amount calculating means A9 are used.

The numerical value converting means A7 calculates the upstream side exhaust air-fuel ratio AFup corresponding to the output current Irup based on the output current Irup of the upstream side air-fuel ratio sensor 40 and a map or calculation formula (for example, the map shown in FIG. 5) which defines the relationship between the output current Irup and the air-fuel ratio of the air-fuel ratio sensor 40. Therefore, the upstream side exhaust air-fuel ratio AFup corresponds to the air-fuel ratio of the exhaust gas flowing into the upstream side exhaust purification catalyst 20.

The air-fuel ratio difference calculating means A8 subtracts the target air-fuel ratio AFT calculated by the target air-fuel ratio setting means A6 from the upstream side exhaust air-fuel ratio AFup calculated by the numerical value converting means A7 to thereby calculate the air-fuel ratio difference DAF (DAF=AFup−AFT). This air-fuel ratio difference DAF is a value which expresses excess/deficiency of the amount of fuel fed with respect to the target air-fuel ratio AFT.

The F/B correction amount calculating means A9 processes the air-fuel ratio difference DAF calculated by the air-fuel ratio difference calculating means A8 by proportional integral derivative processing (PID processing) to thereby calculate the F/B correction amount DFi for compensating for the excess/deficiency of the amount of feed of fuel based on the following equation (1). The thus calculated F/B correction amount DFi is input to the fuel injection calculating means A3.

$$DFi = Kp \cdot DAF + Ki \cdot SDAF + Kd \cdot DDAF \quad (1)$$

Note that, in the above equation (1), Kp is a preset proportional gain (proportional constant), Ki is a preset integral gain (integral constant), and Kd is a preset derivative gain (derivative constant). Further, DDAF is the time derivative value of the air-fuel ratio difference DAF and is calculated by dividing the difference between the currently updated air-fuel ratio difference DAF and the previously updated air-fuel ratio difference DAF by the time corresponding to the updating interval. Further, SDAF is the time derivative value of the air-fuel ratio difference DAF. This time derivative value DDAF is calculated by adding the previously updated time derivative value DDAF and the currently updated air-fuel ratio difference DAF (SDAF=DDAF+DAF).

Note that, in the above embodiment, the air-fuel ratio of the exhaust gas flowing into the upstream side exhaust purification catalyst 20 is detected by the upstream side air-fuel ratio sensor 40. However, the precision of detection of the air-fuel ratio of the exhaust gas flowing into the upstream side exhaust purification catalyst 20 does not necessarily have to be high, and therefore, for example, the air-fuel ratio of the exhaust gas may be estimated based on the fuel injection amount from the fuel injector 11 and output of the air flow meter 39.

<Second Embodiment>

Next, referring to FIG. 11, a control system of an internal combustion engine according to a second embodiment of the present invention will be explained. The configuration and control of the control system of an internal combustion engine in the second embodiment are basically similar to the configuration and control of the control system of an internal combustion engine according to the first embodiment. However, in the control system of the present embodiment, even while the air-fuel ratio adjustment amount AFC is set to the slight rich set adjustment amount AFCrich, every certain extent of time interval, the air-fuel ratio adjustment amount AFC is temporarily set to a value corresponding to the lean air-fuel ratio (for example, lean set adjustment amount AFClean) for a short time. That is, in the control system of the present embodiment, even while the target air-fuel ratio is set to the slight rich set air-fuel ratio, every certain extent of time interval, the target air-fuel ratio is temporarily set to a lean air-fuel ratio for a short time.

Figure 11:
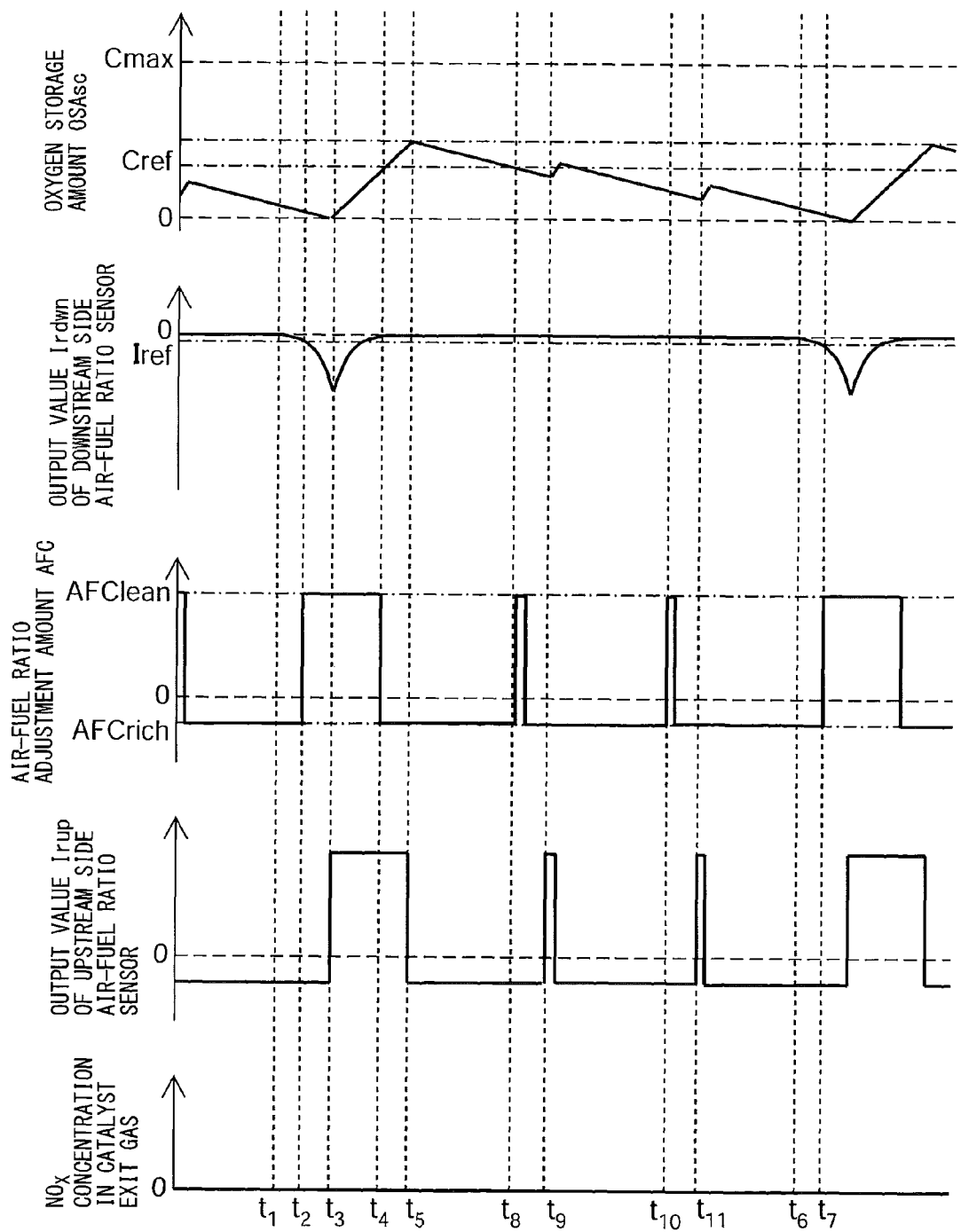
FIG. 11 is a time chart of the oxygen storage amount of the exhaust purification catalyst, etc.

FIG. 11 is a view similar to FIG. 7. In FIG. 11, the times $t_1$ to $t_7$ show timings of control similar to the times $t_1$ to $t_7$ in FIG. 7. Therefore, in the control shown in FIG. 11 as well, at the timings of the times $t_1$ to $t_7$, control similar to the control shown in FIG. 7 is performed. In addition, in the control shown in FIG. 11, between the times $t_4$ to $t_7$, that is, while the air-fuel ratio adjustment amount AFC is set to the slight rich set adjustment amount AFCrich, the air-fuel ratio adjustment amount AFC is temporarily set to the lean set adjustment amount AFClean several times.

In the example shown in FIG. 11, the air-fuel ratio adjustment amount AFC is set to a lean set adjustment amount AFClean over a short time from the time $t_8$. As explained above, a delay occurs in the change of the air-fuel ratio, and therefore the air-fuel ratio of the exhaust gas flowing into the upstream side exhaust purification catalyst 20 is set to a lean air-fuel ratio over a short time from the time $t_9$. In this way, if the air-fuel ratio of the exhaust gas flowing into the upstream side exhaust purification catalyst 20 becomes a lean air-fuel ratio, during that time, the oxygen storage amount OSAsc of the upstream side exhaust purification catalyst 20 temporarily increases.

In the example shown in FIG. 11, similarly, the air-fuel ratio adjustment amount AFC is set to the lean set adjustment amount AFClean over a short time, at the time $t_{10}$. Along with this, the air-fuel ratio of the exhaust gas flowing into the upstream side exhaust purification catalyst 20 becomes a lean air-fuel ratio over a short time from the time $t_{11}$ and, during that time, the oxygen storage amount OSAsc of the upstream side exhaust purification catalyst 20 temporarily increases.

By temporarily increasing the air-fuel ratio of the exhaust gas flowing into the upstream side exhaust purification catalyst 20 in this way, the oxygen storage amount OSAsc of the upstream side exhaust purification catalyst 20 can be temporarily increased or the decrease in the oxygen storage amount OSAsc can be temporarily reduced. Therefore, according to the present embodiment, it is possible to extend the time from when switching the air-fuel ratio adjustment amount AFC to the slight rich set adjustment amount AFCrich at the time $t_4$ to when the output current Irdwn of the downstream side air-fuel ratio sensor 41 reaches the rich judged reference value Iref at the time $t_7$. That is, it is possible to delay the timing at which the oxygen storage amount OSAsc of the upstream side exhaust purification catalyst 20 becomes close to zero and unburned gas flows out from the upstream side exhaust purification catalyst 20. Due to this, it is possible to reduce the amount of outflow of unburned gas from the upstream side exhaust purification catalyst 20.

Note that, in the above embodiment, while the air-fuel ratio adjustment amount AFC is basically set to the slight rich set adjustment amount AFCrich (times $t_4$ to $t_7$), the air-fuel ratio adjustment amount AFC is temporarily set to the lean set adjustment amount AFClean. When temporarily changing the air-fuel ratio adjustment amount AFC in this way, it is not necessarily required to change the air-fuel ratio adjustment amount AFC to the lean set adjustment amount AFClean. The air-fuel ratio may be changed in any way so long as it is leaner than the slight rich set adjustment amount AFCrich.

Further, even while the air-fuel ratio adjustment amount AFC is basically set to the lean set adjustment amount AFClean (times $t_2$ to $t_4$), the air-fuel ratio adjustment amount AFC may temporarily be set to the slight rich set adjustment amount AFCrich. In this case as well, similarly, when temporarily changing the air-fuel ratio adjustment amount AFC, the air-fuel ratio adjustment amount AFC may be changed to any air-fuel ratio so long as one richer than the lean set adjustment amount AFClean.

However, in the present embodiment as well, the air-fuel ratio adjustment amount AFC during the times $t_2$ to $t_4$ is set so that the difference of the average value of the target air-fuel ratio and the stoichiometric air-fuel ratio in that period becomes larger than the difference of the average value of the target air-fuel ratio and the stoichiometric air-fuel ratio during the times $t_4$ to $t_7$.

Whatever the case, if expressing the first embodiment and the second embodiment together, the ECU 31 can be said to comprise: an oxygen storage amount increasing means for continuously or intermittently setting a target air-fuel ratio of exhaust gas flowing into the upstream side catalyst 20 to a lean set air-fuel ratio when the air-fuel ratio of the exhaust gas detected by the downstream side air-fuel ratio sensor 41 becomes a rich judged air-fuel ratio or less, until the oxygen storage amount OSAsc of the upstream side catalyst 20 becomes the judged reference storage amount Cref; and an oxygen storage amount decreasing means for continuously or intermittently setting the target air-fuel ratio to a slight rich set air-fuel ratio when the oxygen storage amount OSAsc of the upstream side catalyst 20 becomes the judged reference storage amount Cref or more so that the oxygen storage amount OSAsc decreases toward zero without reaching the maximum oxygen storage amount Cmax.

<Third Embodiment>

Next, referring to FIGS. 12-17, a control system of an internal combustion engine according to a third embodiment of the present invention will be explained. The configuration and control of the control system of an internal combustion engine according to the third embodiment are basically similar to the configuration and control of the control system of an internal combustion engine according to the above embodiments. However, in the above embodiments, the same applied voltage is applied to both the upstream side air-fuel ratio sensor and the downstream side air-fuel ratio sensor, while in the present embodiment, different applied voltages are applied to these air-fuel ratio sensors.

<Output Characteristic of Air-Fuel Ratio Sensor>

Figure 12:
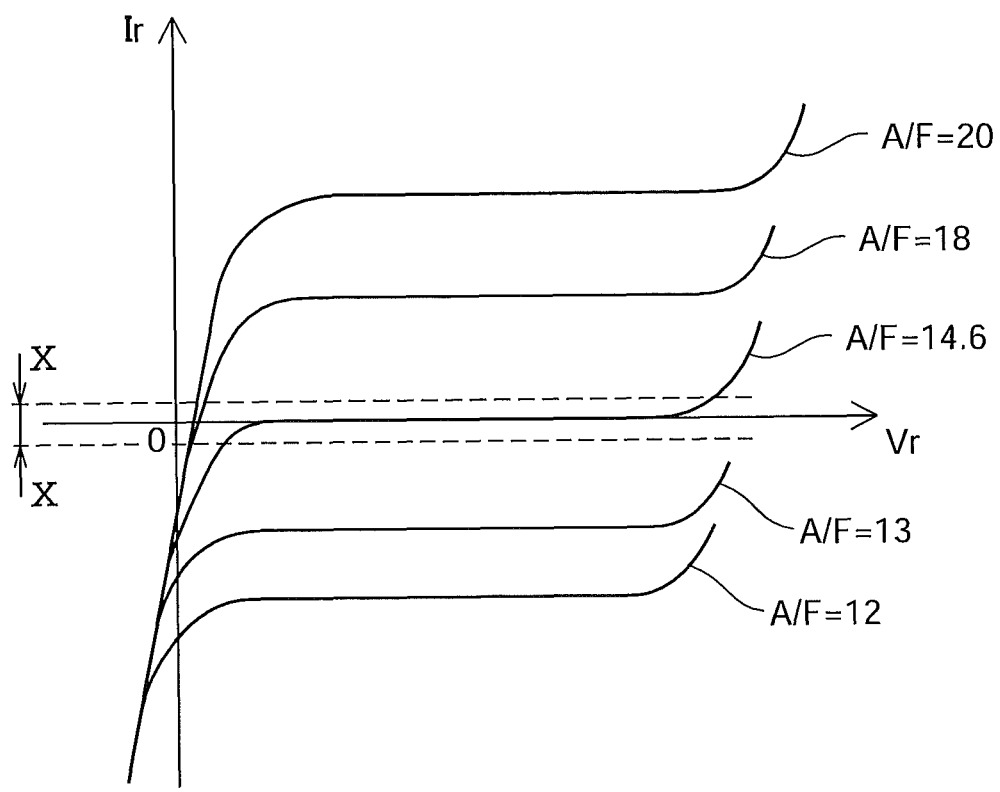
FIG. 12 is a view which shows the relationship between a sensor applied voltage and output current at different the exhaust air-fuel ratios.

The upstream side air-fuel ratio sensor 70 and the downstream side air-fuel ratio sensor 71 of the present embodiment are configured and operated as explained using FIGS. 3 and 4, similarly to the air-fuel ratio sensors 40 and 41 of the first embodiment. These air-fuel ratio sensors 70 and 71 have the voltage-current (V-I) characteristic such as shown in FIG. 12. As will be understood from FIG. 12, in the region where the sensor applied voltage Vr is not more than 0 and near 0, when the exhaust air-fuel ratio is constant, if the sensor applied voltage Vr gradually increases from a negative value, the output current Ir increases along with this.

That is, in this voltage region, since the sensor applied voltage Vr is low, the flow rate of oxygen ions which can move through the solid electrolyte layer 51 is small. For this reason, the flow rate of oxygen ions which can move through the solid electrolyte layer 51 becomes smaller than the rate of inflow of exhaust gas through the diffusion regulating layer 54 and, accordingly, the output current Ir changes in accordance with the flow rate of oxygen ions which can move through the solid electrolyte layer 51. The flow rate of oxygen ions which can move through the solid electrolyte layer 51 changes in accordance with the sensor applied voltage Vr, and, as a result, the output current increases along with the increase in the sensor applied voltage Vr. Note that, the voltage region where the output current Ir changes in proportion to the sensor applied voltage Vr in this way is called the "proportional region". Further, when the sensor applied voltage Vr is 0, the output current Ir becomes a negative value since an electromotive force E according to the oxygen concentration ratio is generated between the two lateral surfaces of the solid electrolyte layer 51, by the oxygen cell characteristic.

Then, if leaving the exhaust air-fuel ratio constant and gradually increasing the sensor applied voltage Vr, the ratio of increase of output current to the increase of the voltage will gradually become smaller and will finally substantially be saturated. As a result, even if increasing the sensor applied voltage Vr, the output current will no longer change much at all. This substantially saturated current is called the "limit current". Below, the voltage region where this limit current occurs will be called the "limit current region".

That is, in this limit current region, the sensor applied voltage Vr is high to a certain extent, and therefore the flow rate of oxygen ions which can move through the solid electrolyte layer 51 is large. Therefore, the flow rate of oxygen ions which can move through the solid electrolyte layer 51 becomes greater than the rate of inflow of exhaust gas through the diffusion regulating layer 54. Therefore, the output current Ir changes in accordance with the concentration of oxygen or concentration of unburned gas in the exhaust gas flowing into the measured gas chamber 57 through the diffusion regulating layer 54. Even if making the exhaust air-fuel ratio constant and changing the sensor applied voltage Vr, basically, the concentration of oxygen or concentration of unburned gas in the exhaust gas flowing into the measured gas chamber 57 through the diffusion regulating layer 54 does not change, and therefore the output voltage Ir does not change.

However, if the exhaust air-fuel ratio differs, the concentration of oxygen and concentration of unburned gas in the exhaust gas flowing into the measured gas chamber 57 through the diffusion regulating layer 54 also differ, and therefore the output current Ir changes in accordance with the exhaust air-fuel ratio. As will be understood from FIG. 12, between the lean air-fuel ratio and the rich air-fuel ratio, the direction of flow of the limit current is opposite. At the time of the lean air-fuel ratio, the absolute value of the limit current becomes larger the larger the air-fuel ratio, while at the time of the rich air-fuel ratio, the absolute value of the limit current becomes larger the smaller the air-fuel ratio.

Then, if holding the exhaust air-fuel ratio constant and further increasing the sensor applied voltage Vr, the output current Ir again starts to increase along with the increase in the voltage. If applying a high sensor applied voltage Vr in this way, the moisture which is contained in the exhaust gas breaks down on the exhaust side electrode 52. Along with this, current flows. Further, if further increasing the sensor applied voltage Vr, even with just breakdown of moisture, the current no longer becomes sufficient. At this time, the solid electrolyte layer 51 breaks down. Below, the voltage region where moisture and the solid electrolyte layer 51 break down in this way will be called the "moisture breakdown region".

Figure 13:
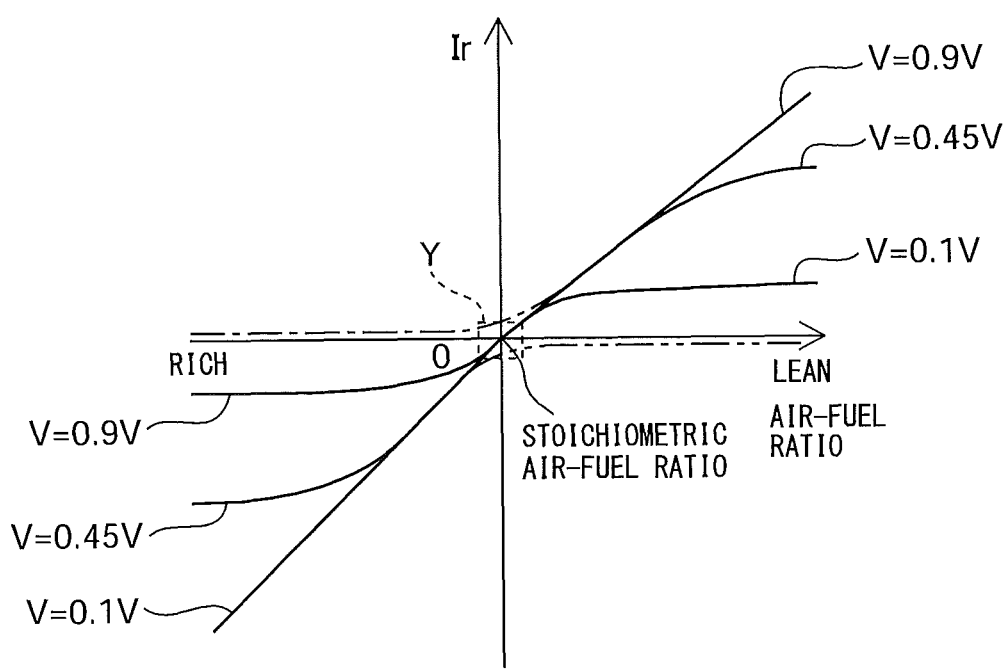
FIG. 13 is a view which shows the relationship between the exhaust air-fuel ratio and output current at different sensor applied voltages.

FIG. 13 is a view which shows the relationship between the exhaust air-fuel ratio and the output current Ir at different sensor applied voltages Vr. As will be understood from FIG. 13, if the sensor applied voltage Vr is 0.1V to 0.9V or so, the output current Ir changes in accordance with the exhaust air-fuel ratio at least near the stoichiometric air-fuel ratio. Further, as will be understood from FIG. 13, if sensor applied voltage Vr is 0.1V to 0.9V or so, near the stoichiometric air-fuel ratio, the relationship between the exhaust air-fuel ratio and the output current Ir is substantially the same regardless of the sensor applied voltage Vr.

On the other hand, as will be understood from FIG. 13, if the exhaust air-fuel ratio becomes lower than a certain exhaust air-fuel ratio or less, the output current Ir no longer changes much at all even if the exhaust air-fuel ratio changes. This certain exhaust air-fuel ratio changes in accordance with the sensor applied voltage Vr. It becomes higher the higher the sensor applied voltage Vr. For this reason, if making the sensor applied voltage Vr increase to a certain specific value or more, as shown in the figure by the one-dot chain line, no matter what the value of the exhaust air-fuel ratio, the output current Ir will no longer become 0.

On the other hand, if the exhaust air-fuel ratio becomes higher than a certain exhaust air-fuel ratio or more, the output current Ir no longer changes much at all even if the exhaust air-fuel ratio changes. This certain exhaust air-fuel ratio also changes in accordance with the sensor applied voltage Vr. It becomes lower the lower the sensor applied voltage Vr. For this reason, if making the sensor applied voltage Vr decrease to a certain specific value or less, as shown in the figure by the two-dot chain line, no matter what the value of the exhaust air-fuel ratio, the output current Ir will no longer become 0 (for example, when the sensor applied voltage Vr is set to 0 V, the output current Ir does not become 0 regardless of the exhaust air-fuel ratio).

<Microscopic Characteristics near Stoichiometric Air-Fuel Ratio>

The inventors of the present invention engaged in in-depth research whereupon they discovered that if viewing the relationship between the sensor applied voltage Vr and the output current Ir (FIG. 12) or the relationship between the exhaust air-fuel ratio and output current Ir (FIG. 13) macroscopically, they trend like explained above, but if viewing these relationships microscopically near the stoichiometric air-fuel ratio, they trend differently from the above. Below, this will be explained.

Figure 14:
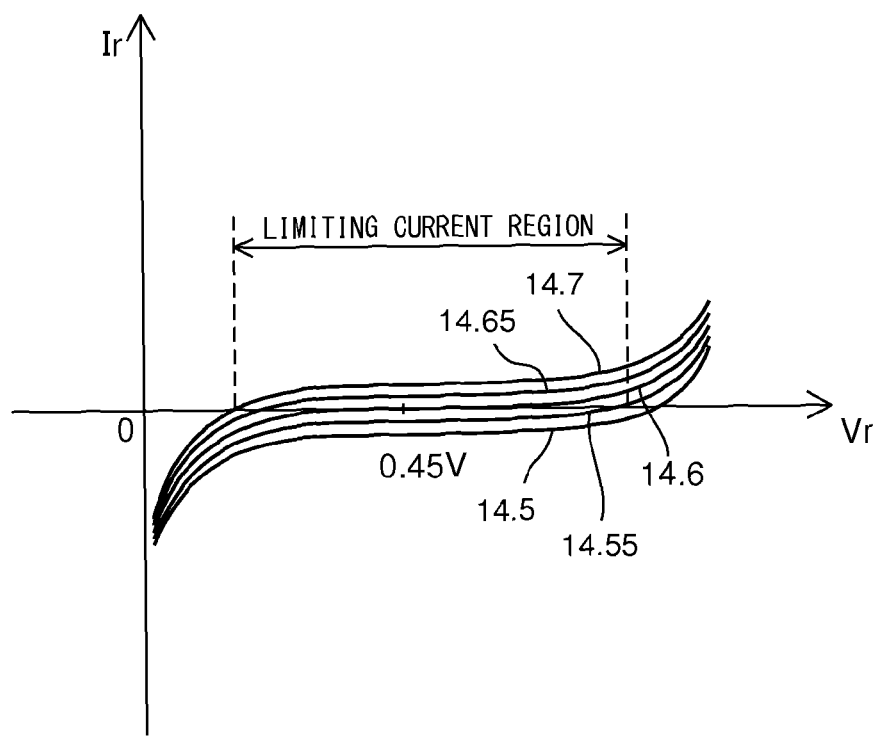
FIG. 14 is a view which shows enlarged the region which is shown by X-X in FIG. 12.

FIG. 14 is a view which shows enlarged the region where the output current Ir becomes near 0 (region shown by X-X in FIG. 12), regarding the voltage-current graph of FIG. 12. As will be understood from FIG. 14, even in the limit current region, when making the exhaust air-fuel ratio constant, the output current Ir also increases, though very slightly, along with the increase in the sensor applied voltage Vr. For example, considering the case where the exhaust air-fuel ratio is the stoichiometric air-fuel ratio (14.6) as an example, when the sensor applied voltage Vr is 0.45V or so, the output current Ir becomes 0. As opposed to this, if setting the sensor applied voltage Vr to lower than 0.45V by a certain extent (for example, 0.2V), the output current becomes a value lower than 0. On the other hand, if setting the sensor applied voltage Vr to higher than 0.45V by a certain extent (for example, 0.7V), the output current becomes a value higher than 0.

Figure 15:
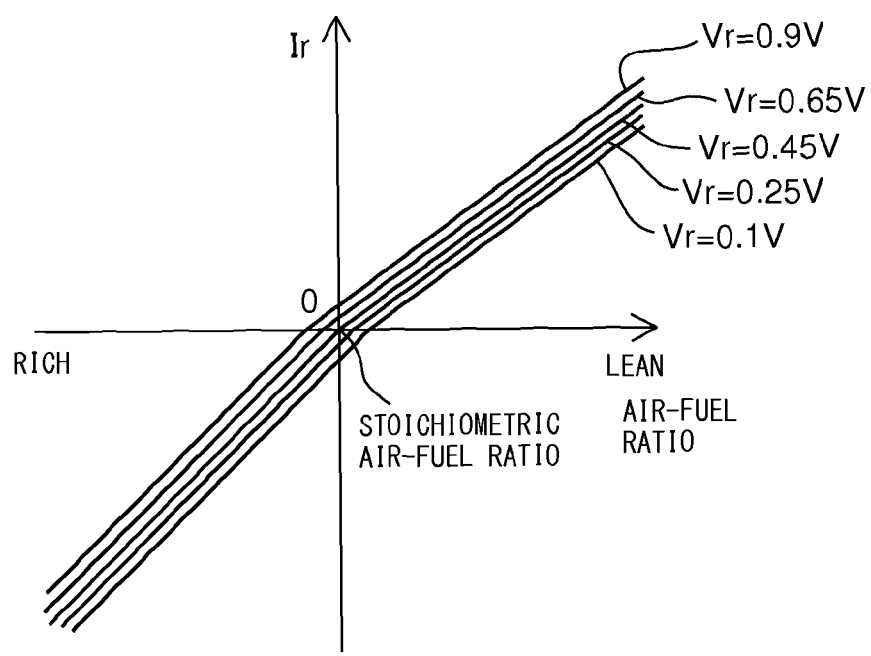
FIG. 15 is a view which shows enlarged the region which is shown by Y in FIG. 13.

FIG. 15 is a view which shows enlarged the region where the exhaust air-fuel ratio is near the stoichiometric air-fuel ratio and the output current Ir is near 0 (region shown by Y in FIG. 13), regarding the air-fuel ratio-current graph of FIG. 13. From FIG. 15, it will be understood that in the region near the stoichiometric air-fuel ratio, the output current Ir for the same exhaust air-fuel ratio slightly differs for each sensor applied voltage Vr. For example, in the illustrated example, when the exhaust air-fuel ratio is the stoichiometric air-fuel ratio, the output current Ir when the sensor applied voltage Vr is 0.45V becomes 0. Further, if setting the sensor applied voltage Vr to larger than 0.45V, the output current Ir also becomes larger than 0. If setting the sensor applied voltage Vr to smaller than 0.45V, the output current Ir also becomes smaller than 0.

In addition, from FIG. 15, it will be understood that the exhaust air-fuel ratio when the output current Ir is 0 (below, referred to as "exhaust air-fuel ratio at the time of zero current") differs for each sensor applied voltage Vr. In the illustrated example, when the sensor applied voltage Vr is 0.45V, the output current Ir becomes 0 when the exhaust air-fuel ratio is the stoichiometric air-fuel ratio. As opposed to this, if the sensor applied voltage Vr is larger than 0.45V, the output current Ir becomes 0 when the exhaust air-fuel ratio is richer than the stoichiometric air-fuel ratio. The larger the sensor applied voltage Vr becomes, the smaller the exhaust air-fuel ratio at the time of zero current. Conversely, if the sensor applied voltage Vr is smaller than 0.45V, the output current Ir becomes 0 when the exhaust air-fuel ratio is leaner than the stoichiometric air-fuel ratio. The smaller the sensor applied voltage Vr, the larger the exhaust air-fuel ratio at the time of zero current. That is, by making the sensor applied voltage Vr change, it is possible to change the exhaust air-fuel ratio at the time of zero current.

In this regard, the slope at FIG. 5, that is, the ratio of the amount of increase of the output current to the amount of increase of the exhaust air-fuel ratio (below, referred to as the "rate of change of the output current"), does not necessarily become the same even through similar production processes. Therefore, even with the same type of air-fuel ratio sensor, variations occur between specimens. In addition, even at the same air-fuel ratio sensor, the rate of change of output current changes due to aging, etc. As a result, even if using the same type of sensor which is configured to have the output characteristic shown by the solid line A in FIG. 16, depending on the sensor used or the time period of use, etc., as shown by the broken line B in FIG. 16, the rate of change of the output current will become small or, as shown by the one-dot chain line C, the rate of change of the output current will become large.

Therefore, even if using the same type of air-fuel ratio sensor to measure exhaust gas of the same air-fuel ratio, depending on the sensor used or the time period of use, etc., the output current of the air-fuel ratio sensor will differ. For example, when the air-fuel ratio sensor has an output characteristic such as shown by the solid line A, the output current when measuring the exhaust gas with an air-fuel ratio of $af_1$ becomes $I_2$. However, when the air-fuel ratio sensor has the output characteristic such as shown by the broken line B or one-dot chain line C, the output currents when measuring the exhaust gas with an air-fuel ratio of $af_1$ become $I_1$ and $I_3$ respectively, that is, output currents different from the above-mentioned $I_2$.

Figure 16:
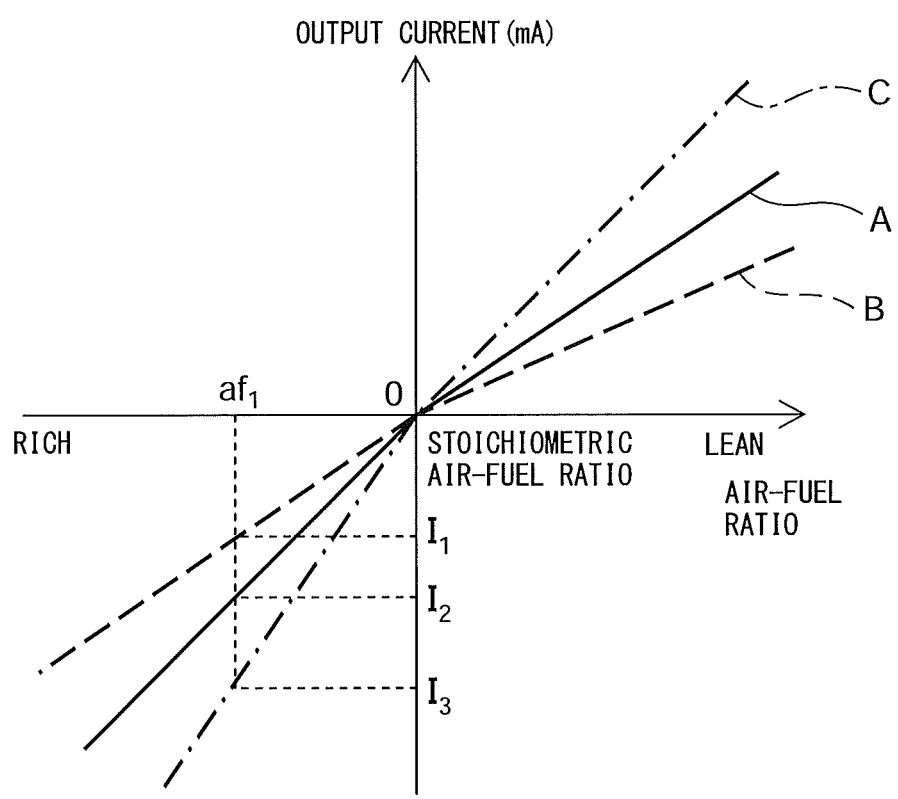
FIG. 16 is a view which shows the relationship between the air-fuel ratio of the air-fuel ratio sensor and the output current.

However, as will be understood from FIG. 16, even if variation occurs between specimens of an air-fuel ratio sensor or variations occur in the same air-fuel ratio sensor due to aging, etc., the exhaust air-fuel ratio at the time of zero current (in the example of FIG. 16, the stoichiometric air-fuel ratio) does not change much at all. That is, when the output current Ir becomes a value other than zero, it is difficult to accurately detect the absolute value of the exhaust air-fuel ratio, while when the output current Ir becomes zero, it is possible to accurately detect the absolute value of the exhaust air-fuel ratio (in the example of FIG. 16, stoichiometric air-fuel ratio).

Further, as explained using FIG. 15, in the air-fuel ratio sensors 70 and 71, by changing the sensor applied voltage Vr, it is possible to change the exhaust air-fuel ratio at the time of zero current. That is, if suitably setting the sensor applied voltage Vr, it is possible to accurately detect the absolute value of an exhaust air-fuel ratio other than the stoichiometric air-fuel ratio. In particular, when changing the sensor applied voltage Vr within a later explained "specific voltage region", it is possible to adjust the exhaust air-fuel ratio at the time of zero current only slightly with respect to the stoichiometric air-fuel ratio (14.6) (for example, within a range of ±1% (about 14.45 to about 14.75)). Therefore, by suitably setting the sensor applied voltage Vr, it becomes possible to accurately detect the absolute value of an air-fuel ratio which slightly differs from the stoichiometric air-fuel ratio.

Note that, by changing the sensor applied voltage Vr, it is possible to change the exhaust air-fuel ratio at the time of zero current. However, if changing the sensor applied voltage Vr so as to be larger than a certain upper limit voltage or smaller than a certain lower limit voltage, the amount of change in the exhaust air-fuel ratio at the time of zero current, with respect to the amount of change in the sensor applied voltage Vr, becomes larger. Therefore, in these voltage regions, if the sensor applied voltage Vr slightly shifts, the exhaust air-fuel ratio at the time of zero current greatly changes. Therefore, in this voltage region, to accurately detect the absolute value of the exhaust air-fuel ratio, it becomes necessary to precisely control the sensor applied voltage Vr. This is not that practical. Therefore, from the viewpoint of accurately detecting the absolute value of the exhaust air-fuel ratio, the sensor applied voltage Vr has to be a value within a "specific voltage region" between a certain upper limit voltage and a certain lower limit voltage.

In this regard, as shown in FIG. 14, the air-fuel ratio sensors 70 and 71 have a limit current region which is a voltage region where the output current Ir becomes a limit current for each exhaust air-fuel ratio. In the present embodiment, the limit current region when the exhaust air-fuel ratio is the stoichiometric air-fuel ratio is defined as the "specific voltage region".

Note that, as explained using FIG. 13, if increasing the sensor applied voltage Vr to a certain specific value (maximum voltage) or more, as shown in the figure by the one-dot chain line, no matter what value the exhaust air-fuel ratio is, the output current Ir will no longer become 0. On the other hand, if decreasing the sensor applied voltage Vr to a certain specific value (minimum voltage) or less, as shown in the figure by the two-dot chain line, no matter what value the exhaust air-fuel ratio, the output current Ir will no longer become 0.

Therefore, if the sensor applied voltage Vr is a voltage between the maximum voltage and the minimum voltage, there is an exhaust air-fuel ratio where the output current becomes zero. Conversely, if the sensor applied voltage Vr is a voltage higher than the maximum voltage or a voltage lower than the minimum voltage, there is no exhaust air-fuel ratio where the output current will become zero. Therefore, the sensor applied voltage Vr at least has to be able to be a voltage where the output current becomes zero when the exhaust air-fuel ratio is any air-fuel ratio, that is, a voltage between the maximum voltage and the minimum voltage. The above-mentioned "specific voltage region" is the voltage region between the maximum voltage and the minimum voltage.

<Applied Voltage at Individual Air-Fuel Ratio Sensors>

In the present embodiment, considering the above-mentioned microscopic characteristics, when detecting the air-fuel ratio of the exhaust gas by the upstream side air-fuel ratio sensor 70, the sensor applied voltage Vrup at the upstream side air-fuel ratio sensor 70 is fixed to a voltage (for example, 0.45V) where the output current becomes zero when the exhaust air-fuel ratio is the stoichiometric air-fuel ratio (in the present embodiment, 14.6). In other words, in the upstream side air-fuel ratio sensor 70, the sensor applied voltage Vrup is set so that the exhaust air-fuel ratio at the time of zero current becomes the stoichiometric air-fuel ratio. On the other hand, when detecting the air-fuel ratio of the exhaust gas by the downstream side air-fuel ratio sensor 71, the sensor applied voltage Vr at the downstream side air-fuel ratio sensor 71 is fixed to a constant voltage (for example, 0.7V) where the output current becomes zero when the exhaust air-fuel ratio is the rich judged air-fuel ratio slightly richer than the stoichiometric air-fuel ratio (for example, 14.55). In other words, in the downstream side air-fuel ratio sensor 71, the sensor applied voltage Vrdwn is set so that exhaust air-fuel ratio at the time of zero current becomes a rich judged air-fuel ratio which is slightly richer than the stoichiometric air-fuel ratio. Accordingly, in the present embodiment, the sensor applied voltage Vrdwn of the downstream side air-fuel ratio sensor 71 is a higher voltage than the sensor applied voltage Vrup of the upstream side air-fuel ratio sensor 70.

Therefore, the ECU 31 connected to the two air-fuel ratio sensors 70 and 71 judges that the exhaust air-fuel ratio around the upstream side air-fuel ratio sensor 70 is the stoichiometric air-fuel ratio when the output current Irup of the upstream side air-fuel ratio sensor 70 becomes zero. On the other hand, the ECU 31 judges that the exhaust air-fuel ratio around the downstream side air-fuel ratio sensor 71 is the lean judged air-fuel ratio, that is, is a predetermined air-fuel ratio leaner than the stoichiometric air-fuel ratio, when the output current Irdwn of the downstream side air-fuel ratio sensor 71 becomes zero.

<Air-Fuel Ratio Control in Third Embodiment>

The air-fuel ratio control in the third embodiment is basically similar to the air-fuel ratio control in the above embodiments. However, in the first embodiment, when at the time $t_2$ the output current Irdwn of the downstream side air-fuel ratio sensor 41 becomes the rich judgment reference value Iref or less, the target air-fuel ratio is switched to the lean set air-fuel ratio. As opposed to this, in the present embodiment, when the output current Irdwn of the downstream side air-fuel ratio sensor 41 becomes zero or less, the target air-fuel ratio is switched to the lean set air-fuel ratio.

Figure 17:
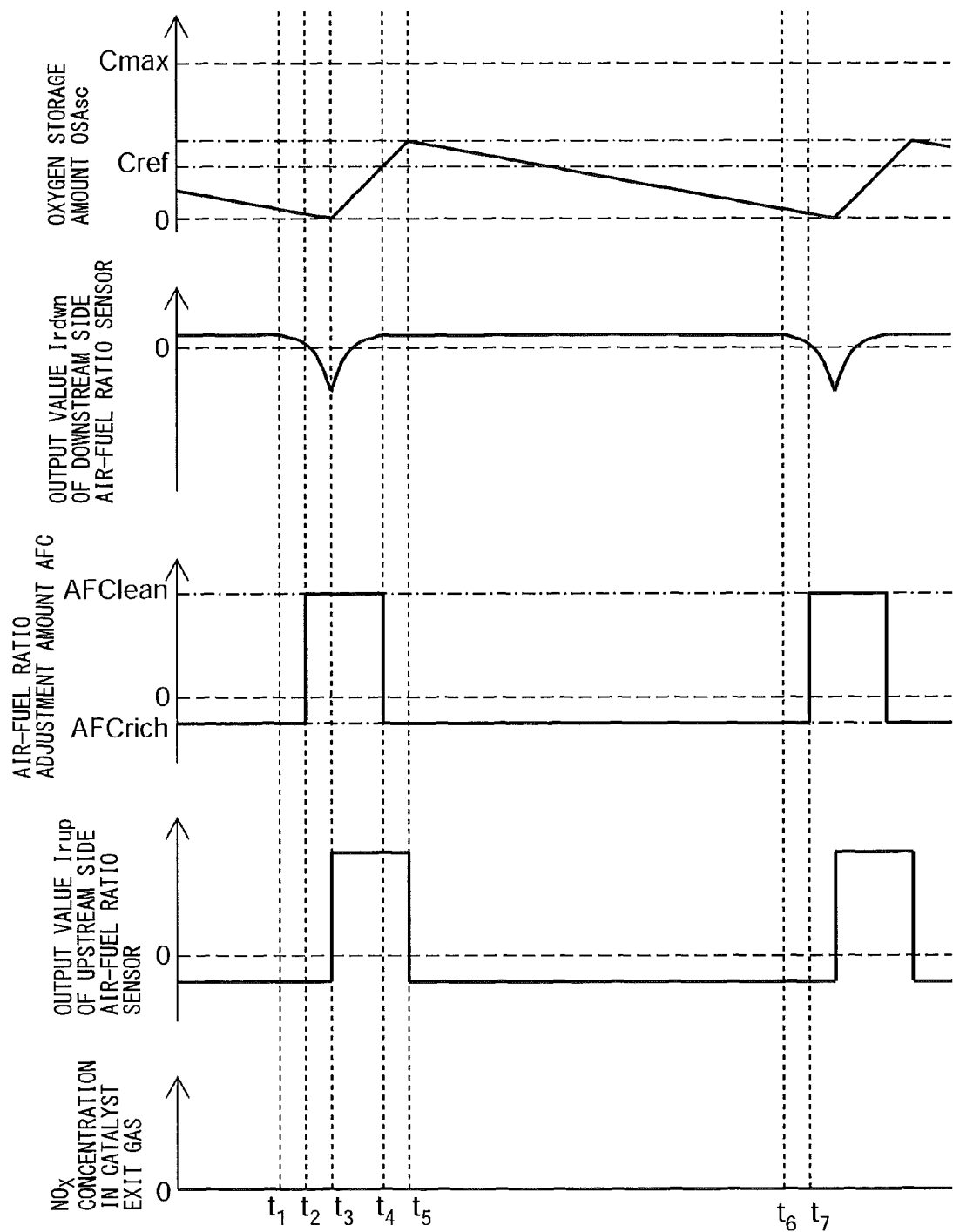
FIG. 17 is a time chart of the oxygen storage amount of the exhaust purification catalyst, etc.

FIG. 17 is a view similar to FIG. 7 and is a time chart of the oxygen storage amount OSAsc of the upstream side exhaust purification catalyst 20, etc., in the case of performing control in the present embodiment. Below, only parts which differ from the control in FIG. 7 will be explained.

As will be understood from FIG. 17, before the time $t_1$, that is, when the air-fuel ratio of the exhaust gas flowing out from the upstream side exhaust purification catalyst 20 is the stoichiometric air-fuel ratio, the output current Irdwn of the downstream side air-fuel ratio sensor 71 becomes a value larger than zero. Then, part of the unburned gas in the exhaust gas flowing into the upstream side exhaust purification catalyst 20 starts to flow out without being removed at the upstream side exhaust purification catalyst 20, from the time $t_1$. Along with this, the output current Irdwn of the downstream side air-fuel ratio sensor 71 becomes smaller toward zero and becomes zero at the time $t_2$. In the present embodiment, if the output current Irdwn of the downstream side air-fuel ratio sensor 71 becomes zero or less, in order to suppress the decrease in the oxygen storage amount OSAsc of the upstream side exhaust purification catalyst 20, the air-fuel ratio adjustment amount AFC is switched to a value AFClean which corresponds to the lean set air-fuel ratio. The control after that is basically similar to the example shown in FIG. 7.

According to the present embodiment, as explained above, the absolute value at the rich judged air-fuel ratio can be accurately detected by the downstream side air-fuel ratio sensor 41. As explained using FIG. 16, with a conventional air-fuel ratio sensor, it was difficult to accurately detect the absolute value of the air-fuel ratio other than the stoichiometric air-fuel ratio. Therefore, if error occurs in the output current in a conventional air-fuel ratio sensor due to aging, individual differences, etc., even when the actual air-fuel ratio of the exhaust gas differs from the rich judged air-fuel ratio, the output current of the air-fuel ratio sensor may be a value corresponding to the rich judged air-fuel ratio. As a result, the timing of switching the air-fuel ratio adjustment amount AFC from the slight rich set adjustment amount AFCrich to the lean set adjustment amount AFClean becomes delayed or this switching is performed at a time when switching is unnecessary. As opposed to this, in the present embodiment, it is possible for the downstream side air-fuel ratio sensor 41 to accurately detect the absolute value of the rich judged air-fuel ratio. Therefore, delay in the timing of switching the air-fuel ratio adjustment amount AFC from the slight rich set adjustment amount AFCrich to the lean set adjustment amount AFClean or switching at a time when switching is unnecessary can be suppressed.

<Fourth Embodiment>

Next, referring to FIGS. 18 and 19, a control system of an internal combustion engine according to a fourth embodiment of the present invention will be explained. The configuration and control of the control system of an internal combustion engine according to the fourth embodiment are basically similar to the configurations and controls of the control systems of internal combustion engines according to the above embodiments. However, in the above embodiments, a single-cell type air-fuel ratio sensor comprised of one cell made of a solid electrolyte layer and a pair of electrodes was used as the air-fuel ratio sensor, while in the fourth embodiment, a two-cell type air-fuel ratio sensor comprised of two such cells is used as the air-fuel ratio sensor.

<Configuration of Air-Fuel Ratio Sensors>

Figure 18:
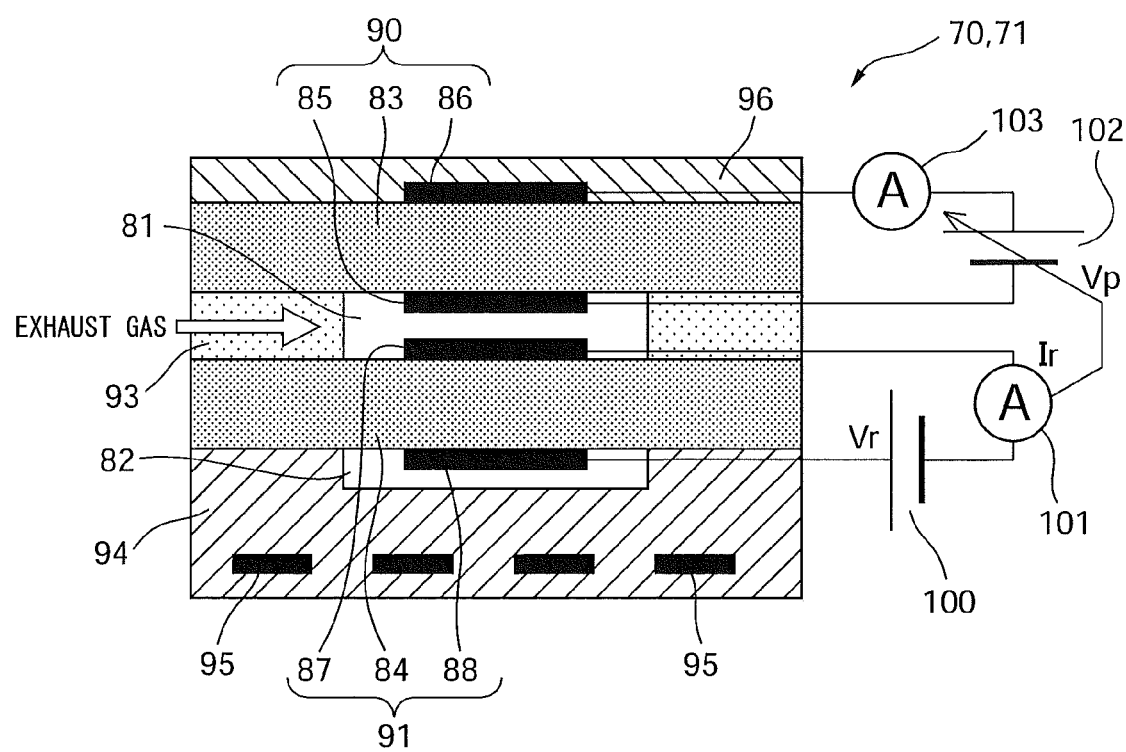
FIG. 18 is a schematic cross-sectional view of an air-fuel ratio sensor of the third embodiment.
Figure 19:
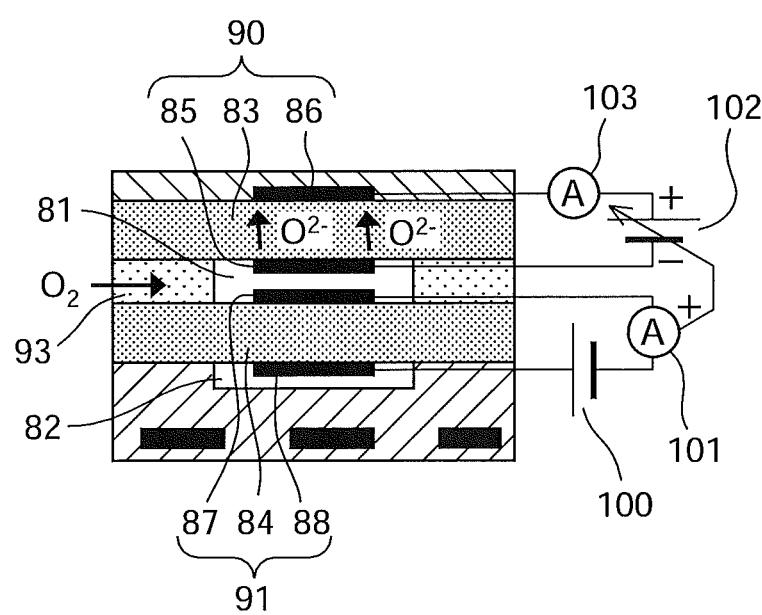
FIG. 19 is a view which schematically shows an operation of an air-fuel ratio sensor of the third embodiment.
Figure 19:
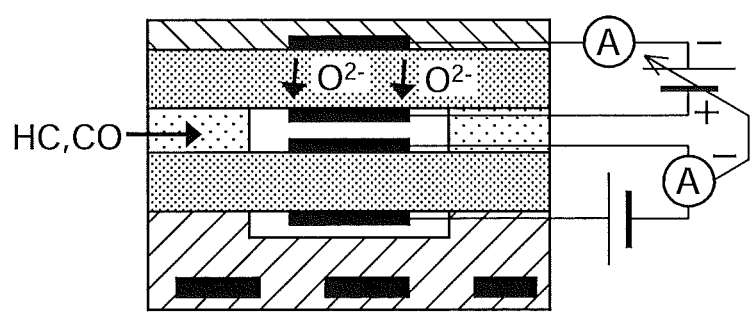
Figure 19:
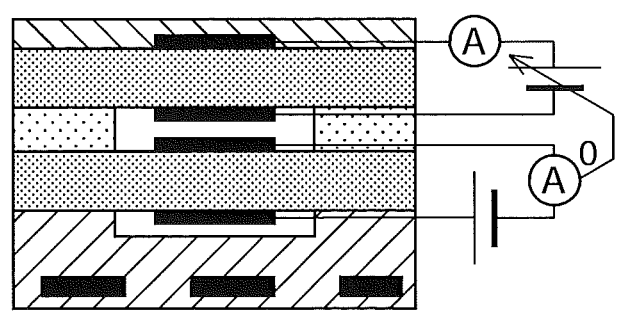
Figure 20:
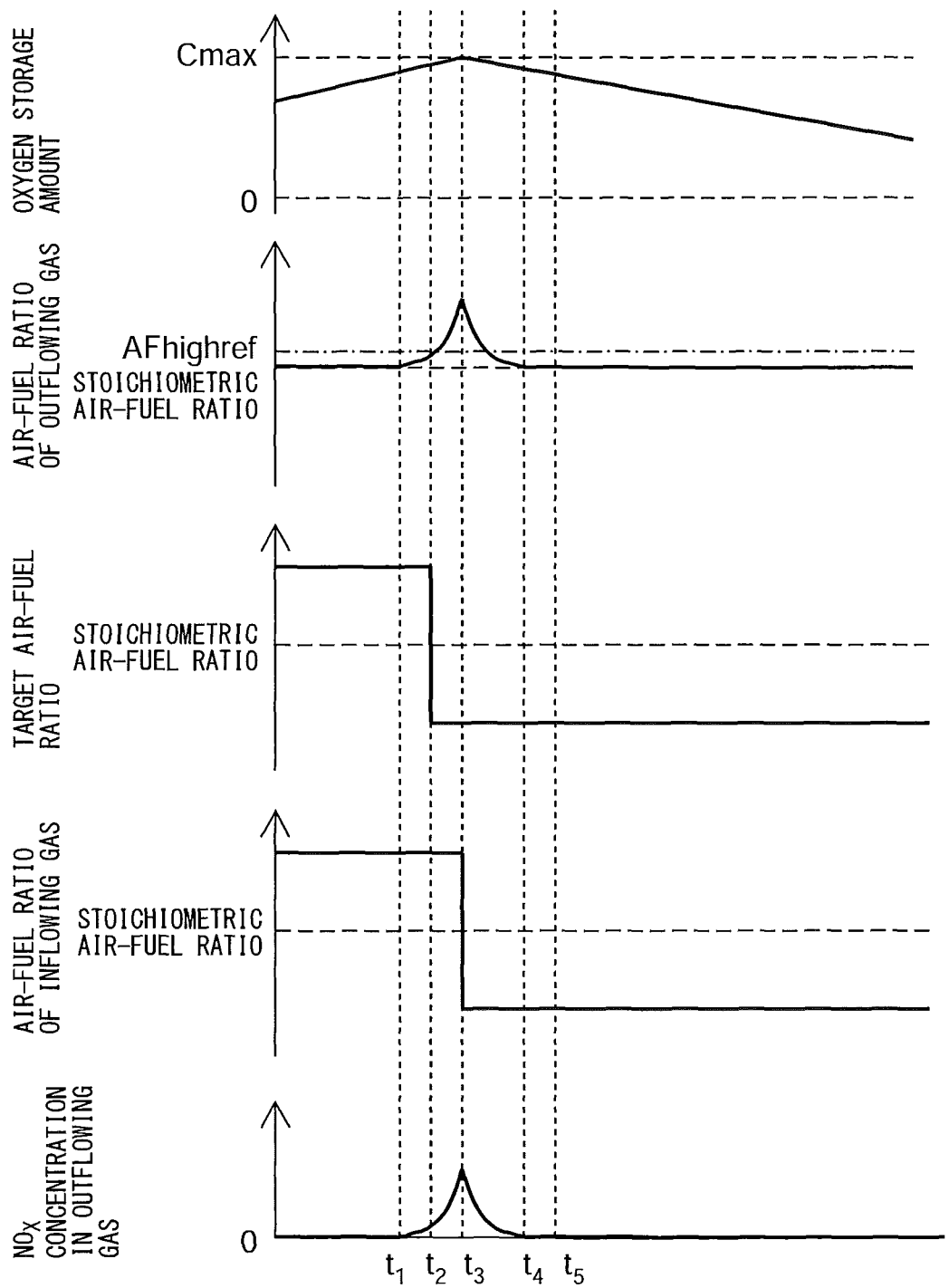
FIG. 20 is a time chart of the oxygen storage amount of the exhaust purification catalyst.

Referring to FIG. 18, the configuration of the air-fuel ratio sensors 70 and 71 in the present embodiment will be explained. FIG. 18 is a schematic cross-sectional view of the air-fuel ratio sensors 70 and 71. As will be understood from FIG. 18, the air-fuel ratio sensors 70 and 71 in the present embodiment are double-cell types of air-fuel ratio sensors, which have two cells each comprised of a solid electrolyte layer and a pair of electrodes.

As shown in FIG. 18, each of the air-fuel ratio sensors 70, 71 comprises a measured gas chamber 81, a reference gas chamber 82, and two solid electrolyte layers 83, 84 which are arranged at the both sides of the measured gas chamber 8. The reference gas chamber 82 is provided at the opposite side of the measured gas chamber 81 across the second solid electrolyte layer 84. On the lateral surface of the first solid electrolyte layer 83 at the measured gas chamber 81 side, a gas chamber side electrode (third electrode) 85 is arranged, while on the lateral surface of the first solid electrolyte layer 83 at the exhaust gas side, an exhaust side electrode (fourth electrode) 86 is arranged. These first solid electrolyte layer 83, gas chamber side electrode 85, and exhaust side electrode 86 configure a pump cell 90.

On the other hand, on the lateral surface of the second solid electrolyte layer 84 at the measured gas chamber 81 side, a gas chamber side electrode (first electrode) 87 is arranged, while on the lateral surface of the second solid electrolyte layer 84 at the reference gas chamber 82 side, a reference side electrode (second electrode) 88 is arranged. These second solid electrolyte layer 84, gas chamber side electrode 87, and reference side electrode 88 configure a reference cell 91.

Between the two solid electrolyte layers 83 and 84, a diffusion regulating layer 93 is provided so as to surround the gas chamber side electrode 85 of the pump cell 90 and the gas chamber side electrode 87 of the reference cell 91. Therefore, the measured gas chamber 81 is defined by the first solid electrolyte layer 83, the second solid electrolyte layer 84, and the diffusion regulating layer 93. Into the measured gas chamber 81, exhaust gas flows through the diffusion regulating layer 93. Accordingly, the electrodes arranged in the measured gas chamber 81, that is, the gas chamber side electrode 85 of the pump cell 90 and the gas chamber side electrode 87 of the reference cell 91, are exposed through the diffusion regulating layer 93 to the exhaust gas. Note that, the diffusion regulating layer 93 does not necessarily have to be provided so that exhaust gas flowing into the measured gas chamber 81 can pass through the diffusion regulating layer 93. So long as the exhaust gas which reaches the gas chamber side electrode 87 of the reference cell 91 is exhaust gas which passes through the diffusion regulating layer, the diffusion regulating layer may be arranged in any manner.

Further, on the lateral surface of the second solid electrolyte layer 84 at the reference gas chamber 82 side, a heater part 94 is provided so as to surround the reference gas chamber 82. Therefore, the reference gas chamber 82 is defined by the second solid electrolyte layer 84 and the heater part 94. In this reference gas chamber 82, reference gas is introduced. In the present embodiment, the reference gas chamber 82 is opened to the atmosphere. Accordingly, inside the reference gas chamber 82, atmospheric air is introduced as reference gas.

Further, the heater part 94 is provided with a plurality of heaters 95. These heaters 95 can be used to control the temperature of the air-fuel ratio sensors 70, 71, in particular the temperature of the solid electrolyte layers 83, 84. The heater part 94 has a sufficient heat generating capacity for heating the solid electrolyte layers 83, 84 until activating. In addition, on the lateral surface of the first solid electrolyte layer 83 at the exhaust gas side, a protective layer 96 is provided. The protective layer 96 is formed from a porous material so that liquid in the exhaust gas, etc., is prevented from directly sticking to the exhaust side electrode 86 while the exhaust gas reaches the exhaust side electrode 86.

The solid electrolyte layers 83, 84 are formed by similar materials to the solid electrolyte layer 51 of the first embodiment. Further, the diffusion regulating layer 93 is also formed by a similar material to the diffusion regulating layer 54 of the first embodiment. Furthermore, the electrodes 85 to 88 are also formed by similar materials to the electrodes 52, 53 of the first embodiment.

Across the gas chamber side electrode 87 and the reference side electrode 88 of the reference cell 91, a reference voltage (corresponding to sensor applied voltage of first embodiment) Vr is applied by the reference voltage application device 100 which is mounted in the ECU 31. In addition, the ECU 31 is provided with a reference current detection device 101 which detects the reference current Ir flowing across these electrodes 87, 88 through the second solid electrolyte layer 84 when the reference voltage application device 100 applies the reference voltage Vr.

Further, between the gas chamber side electrode 85 and the exhaust side electrode 86 of the pump cell 90, pump voltage Vp is applied by a pump voltage application device 102 which is mounted in the ECU 31. The pump voltage Vp applied by the pump voltage application device 102 is set in accordance with the reference current Ir detected by the reference current detection device 101. Specifically, the pump voltage Vp is set in accordance with the difference between the reference current Ir detected by the reference current detection device 101 and the preset target current (in the present embodiment, zero). In addition, the ECU 31 is provided with a pump current detection device 103 which detects a pump current Ip which flows across these electrodes 85 and 86 through the first solid electrolyte layer 83 when the pump voltage application device 102 applies the pump voltage Vp.

Note that, if the pump voltage application device 102 changes the pump voltage Vp, the pump current Ip which flows across the electrodes 85, 86 changes. In other words, the pump voltage application device 102 can be said to control the pump current Ip. Therefore, the pump voltage application device 102 acts as a pump current control device which controls the pump current Ip. Note that, the pump current Ip, for example, changes by arranging a variable resistor in series with the pump voltage application device 102 and changing this variable resistor. Therefore, as the pump current control device, a variable resistor or other means other than the pump voltage application device 102 may be used.

<Operation of Air-Fuel Ratio Sensors>

Next, referring to FIG. 19, the basic concept of the operation of each of the thus configured air-fuel ratio sensors 70, 71 will be explained. FIG. 19 is a view which schematically shows the operation of the air-fuel ratio sensor 70 or 71. At the time of use, the air-fuel ratio sensor 70 or 71 is arranged so that the outer circumferential surfaces of the protection layer 96 and diffusion regulating layer 93 are exposed to the exhaust gas. Further, atmospheric air is introduced into the reference gas chamber 82 of the air-fuel ratio sensor 70 or 71.

As explained above, the solid electrolyte layers 83, 84 are formed by sintered bodies of an oxygen ion conductive oxide. Therefore, they have the property of an electromotive force E being generated which makes oxygen ions move from the high concentration lateral surface side to the low concentration lateral surface side if a difference occurs in the oxygen concentration between the two lateral surfaces of the solid electrolyte layers 83, 84 in the state activated by the high temperature (oxygen cell characteristic).

Conversely, the solid electrolyte layers 83, 84 have the characteristic of trying to make the oxygen ions move so that a ratio of oxygen concentration occurs between the two lateral surfaces of the solid electrolyte layer in accordance with the potential difference, if a potential difference is given between the two lateral surfaces (oxygen pump characteristic). Specifically, when a potential difference is given across the two lateral surfaces, movement of oxygen ions is caused so that the oxygen concentration at the lateral surface to which a positive polarity is given becomes higher than the oxygen concentration at the lateral surface to which a negative polarity is given, by a ratio according to the potential difference.

Therefore, at the pump cell 90, if the pump voltage application device 102 applies the pump voltage Vp across the gas chamber side electrode 85 and the exhaust side electrode 86, movement of oxygen ions occurs corresponding to this. Along which such movement of oxygen ions, oxygen is pumped into or pumped out of the exhaust gas in the measured gas chamber 81.

On the other hand, the reference cell 91 in the present embodiment functions in the same way as the cell in the first embodiment which is comprised of the solid electrolyte layer 51, exhaust side electrode 52, and atmosphere side electrode 53. Therefore, in the reference cell 91, when the exhaust air-fuel ratio in the measured gas chamber 81 conforms to the air-fuel ratio which corresponds to the reference voltage Vr which is applied by the reference voltage application device 100 across the electrodes 87, 88 (that is, the exhaust air-fuel ratio at the time of zero current when applying the reference voltage Vr), the reference current flowing across the electrodes 87, 88 becomes zero. On the other hand, when the exhaust air-fuel ratio in the measured gas chamber 81 is richer than the air-fuel ratio which corresponds to the reference voltage Vr, the reference current flowing across the electrodes 87, 88 becomes a negative current with a magnitude which is proportional to the difference from the air-fuel ratio which corresponds to the reference voltage Vr. Conversely, when the exhaust air-fuel ratio in the measured gas chamber 81 is leaner than the air-fuel ratio which corresponds to the reference voltage Vr, the reference current which flows across the electrodes 87, 88 becomes a positive current with a magnitude which is proportional to the difference from the air-fuel ratio which corresponds to the reference voltage Vr.

When the exhaust air-fuel ratio around the air-fuel ratio sensors 70, 71 is leaner than the air-fuel ratio which corresponds to the reference voltage Vr, as shown in FIG. 19(A), exhaust gas which is leaner than the air-fuel ratio corresponding to the reference voltage Vr flows into each measured gas chamber 81 through the diffusion regulating layer 93. If a lean air-fuel ratio exhaust gas containing such a large amount of oxygen flows in, a positive reference current will flow across the electrodes 87, 88 of the reference cell 91 proportional to the difference from the air-fuel ratio corresponding to the reference voltage Vr, and this reference current will be detected by the reference current detection device 101.

If the reference current detection device 101 detects the reference current, based on this, the pump voltage application device 102 applies pump voltage to the electrodes 85, 86 of the pump cell 90. In particular, if the reference current detection device 101 detects a positive reference current, pump voltage is applied using the exhaust side electrode 86 as the positive electrode and the gas chamber side electrode 85 as the negative electrode. By applying pump voltage to the electrodes 85, 86 of the pump cell 90 in this way, at the first solid electrolyte layer 83 of the pump cell 90, movement of oxygen ions will occur from the negative electrode to the positive electrode, that is, from the gas chamber side electrode 85 toward the exhaust side electrode 86. For this reason, the oxygen inside the measured gas chamber 81 is pumped out into the exhaust gas around the air-fuel ratio sensors 70, 71.

The flow rate of oxygen pumped out from inside each measured gas chamber 81 to the exhaust gas around the air-fuel ratio sensors 70, 71 is proportional to the pump voltage. Further, the pump voltage is proportional to the magnitude of the positive reference current detected by the reference current detection device 101. Therefore, the larger the deviation of the exhaust air-fuel ratio in the measured gas chamber 81 to the lean side from the air-fuel ratio corresponding to the reference voltage Vr, that is, the higher the concentration of oxygen in the measured gas chamber 81, the greater the flow rate of oxygen pumped out from the inside of the measured gas chamber 81 into the exhaust gas around the air-fuel ratio sensors 70, 71. As a result, the flow rate of oxygen flowing through the diffusion regulating layer 93 into the measured gas chamber 81 and the flow rate of oxygen pumped out by the pump cell 90 basically conform to each other. Therefore, the air-fuel ratio in the measured gas chamber 81, is basically maintained substantially at the air-fuel ratio corresponding to the reference voltage Vr.

The flow rate of oxygen pumped by the pump cell 90 equals the flow rate of oxygen ions which move through the inside of the first solid electrolyte layer 83 of the pump cell 90. Further, the flow rate of the oxygen ions is equal to the current which flows across the electrodes 85, 86 of the pump cell 90. Accordingly, by detecting the current flowing across the electrodes 85, 86 by the pump current detection device 103, it is possible to detect the flow rate of oxygen flowing through the diffusion regulating layer 93 into the measured gas chamber 81, and thus a lean air-fuel ratio of the exhaust gas around the measured gas chamber 81.

On the other hand, when the exhaust air-fuel ratio around the air-fuel ratio sensors 70, 71 is richer than the air-fuel ratio corresponding to the reference voltage Vr, as shown in FIG. 19(B), exhaust gas, which is richer than the air-fuel ratio corresponding to the reference voltage Vr, will flow into the measured gas chamber 81 through the diffusion regulating layer 93. If the rich air-fuel ratio exhaust gas containing a large amount of unburned gas flows in like this way, across the electrodes 87, 88 of the reference cell 91, a negative reference current will flow proportional to the difference from the air-fuel ratio corresponding to the reference voltage Vr. This reference current is detected by the reference current detection device 101.

If the reference current detection device 101 detects the reference current, based on this, a pump voltage is applied across the electrodes 85, 86 of the pump cell 90 by the pump voltage application device 102. In particular, if the reference current detection device 101 detects a negative reference current, pump voltage is applied using the gas chamber side electrode 85 as the positive electrode and the exhaust side electrode 86 as the negative electrode. By applying the pump voltage in this way, in the first solid electrolyte layer 83 of the pump cell 90, movement of oxygen ions occurs from the negative electrode to the positive electrode, that is, from the exhaust side electrode 86 toward the gas chamber side electrode 85. For this reason, the oxygen in the exhaust gas around the air-fuel ratio sensors 70, 71 is pumped into the measured gas chamber 81.

The flow rate of oxygen pumped from the exhaust gas around the air-fuel ratio sensors 70, 71 into each measured gas chamber 81 is proportional to the pump voltage. Further, the pump voltage is proportional to the magnitude of the negative reference current detected by the reference current detection device 101. Therefore, the larger the deviation of the exhaust air-fuel ratio in the measured gas chamber 81 to the rich side from the air-fuel ratio corresponding to the reference voltage Vr, that is, the higher the concentration of unburned gas in the measured gas chamber 81, the greater the flow rate of oxygen pumped into the measured gas chamber 81 from the exhaust gas around the air-fuel ratio sensors 70, 71. As a result, the flow rate of unburned gas flowing through the diffusion regulating layer 93 into the measured gas chamber 81 and the flow rate of oxygen pumped in by the pump cell 90 become a chemical equivalent ratio and, accordingly, the air-fuel ratio in of the measured gas chamber 81 is basically maintained at the air-fuel ratio corresponding to the reference voltage Vr.

The flow rate of oxygen pumped in by the pump cell 90 is equal to the flow rate of oxygen ions which move through the inside of the first solid electrolyte layer 83 in the pump cell 90. Further, this flow rate of oxygen ions is equal to the current which flows across the electrodes 85, 86 of the pump cell 90. Accordingly, by detecting the current flowing between the electrodes 85 and 86 by the pump current detection device 103, it is possible to detect the flow rate of unburned gas flowing through the diffusion regulating layer 93 into the measured gas chamber 81 and thus the rich air-fuel ratio of the exhaust gas around the measured gas chamber 81.

Further, when the exhaust air-fuel ratio around the air-fuel ratio sensors 70, 71 is an air-fuel ratio corresponding to the reference voltage Vr, as shown in FIG. 19(C), exhaust gas of an air-fuel ratio which corresponds to the reference voltage Vr flows into the measured gas chamber 81 through the diffusion regulating layer 93. If exhaust gas of an air-fuel ratio which corresponds to the reference voltage Vr flows in like in this way, the reference current flowing across the electrodes 87, 88 of the reference cell 91 becomes zero and the reference current is detected by the reference current detection device 101.

If the reference current detected by the reference current detection device 101 is zero, along with this, the pump voltage applied by the pump voltage application device 102 is also zero. Therefore, in the first solid electrolyte layer 83 of the pump cell 90, no movement of oxygen ions occurs, and accordingly the inside of the measured gas chamber 81 is basically held at the air-fuel ratio corresponding to the reference voltage Vr. Further, no movement of oxygen ions occurs in the first solid electrolyte layer 83 of the pump cell 90, and therefore the pump current detected by the pump current detection device 103 also becomes zero. Therefore, when the pump current detected by the pump current detection device 103 is zero, it is learned that the air-fuel ratio of the exhaust gas around the measured gas chamber 81 is the air-fuel ratio corresponding to the reference voltage Vr.

In this way, according to each of the air-fuel ratio sensors 70, 71 of the present embodiment, when the exhaust air-fuel ratio around the air-fuel ratio sensors 70, 71 conforms to the air-fuel ratio corresponding to the reference voltage Vr, the pump current, which is the output current, becomes zero. Further, when the exhaust air-fuel ratio around the air-fuel ratio sensors 70, 71 is leaner than the air-fuel ratio corresponding to the reference voltage Vr, the pump current, which is the output current, becomes positive, and the absolute value of the pump current becomes larger in accordance with the extent of leanness. Conversely, when the exhaust air-fuel ratio around the air-fuel ratio sensors 70, 71 is richer than the air-fuel ratio corresponding to the reference voltage Vr, the pump current, which is the output current, becomes negative, and the absolute value of the pump current becomes smaller in accordance with the extent of richness.

In addition, the air-fuel ratio corresponding to the reference voltage Vr, that is, the exhaust air-fuel ratio at the time of zero current when applying the reference voltage Vr, as explained in relation to the air-fuel ratio sensors 40, 41 of the above first embodiment, becomes smaller as the reference voltage Vr increases. For example, when the reference voltage Vr is 0.45V, the exhaust air-fuel ratio at the time of zero current becomes the stoichiometric air-fuel ratio. Further, when the reference voltage Vr is larger than 0.45V, the exhaust air-fuel ratio at the time of zero current becomes a rich air-fuel ratio, while when the reference voltage Vr is smaller than 0.45V, the exhaust air-fuel ratio at the time of zero current becomes a lean air-fuel ratio.

<Applied Voltage at Individual Air-Fuel Ratio Sensors>

In the present embodiment, the reference voltage Vrup at the upstream side air-fuel ratio sensor 40 is set to a voltage (for example, 0.45 V) whereby the output current becomes zero when the exhaust air-fuel ratio is the stoichiometric air-fuel ratio (in the present embodiment, 14.6). In other words, in the upstream side air-fuel ratio sensor 40, the reference voltage Vrup is set so that the exhaust air-fuel ratio at the time of zero current becomes the stoichiometric air-fuel ratio. On the other hand, the reference voltage Vrdwn at the downstream side air-fuel ratio sensor 41 is set to a voltage (for example, 0.7V) whereby the output current becomes zero when the exhaust air-fuel ratio is a predetermined rich judged air-fuel ratio (for example, 14.55), which is slightly richer than the stoichiometric air-fuel ratio. In other words, at the downstream side air-fuel ratio sensor 41, the reference voltage Vrdwn is set so that the exhaust air-fuel ratio at the time of zero current becomes a rich judged air-fuel ratio, which is slightly richer than the stoichiometric air-fuel ratio. In this way, in the present embodiment, the reference voltage Vrdwn at the downstream side air-fuel ratio sensor 41 is set to a voltage higher than the reference voltage Vrup at the upstream side air-fuel ratio sensor 40.

Therefore, the ECU 31 which is connected to the both air-fuel ratio sensors 70, 71 judges that the exhaust air-fuel ratio around the upstream side air-fuel ratio sensor 40 is the stoichiometric air-fuel ratio, when the output current of the upstream side air-fuel ratio sensor 40, that is, the pump current Ipup, becomes zero. On the other hand, the ECU 31 judges that the exhaust air-fuel ratio around the downstream side air-fuel ratio sensor 41 is a rich judged air-fuel ratio, that is, a predetermined air-fuel ratio which is different from the stoichiometric air-fuel ratio, when the output current of the downstream side air-fuel ratio sensor 41, that is, the pump current Ipdwn, has become zero.

Note that, in the above third embodiment, both of the upstream side air-fuel ratio sensor and the downstream side air-fuel ratio sensor are single-cell types of air-fuel ratio sensors, while in the above fourth embodiment, both of the upstream side air-fuel ratio sensor and the downstream side air-fuel ratio sensor are double-cell types of air-fuel ratio sensors. However, it is also possible to use a double-cell type of air-fuel ratio sensor as the upstream side air-fuel ratio sensor, and use a single-cell type of air-fuel ratio sensor as the downstream side air-fuel ratio sensor. Conversely, it is also possible to use a single-cell type of air-fuel ratio sensor as the upstream side air-fuel ratio sensor, and use a double-cell type of air-fuel ratio sensor as the downstream side air-fuel ratio sensor. Even in this case, the sensor applied voltage (reference voltage) Vrup at the downstream side air-fuel ratio sensor 41 is set to a voltage which is higher than the sensor applied voltage (reference voltage) Vrdwn at the upstream side air-fuel ratio sensor 40.

In addition, it is also possible to use two-cell type air-fuel ratio sensors for both of the upstream side air-fuel ratio sensor and the downstream side air-fuel ratio sensor while, in the same way as the first embodiment, making the reference voltage Vr at the two air-fuel ratio sensors the same. In this case, when the pump current Ip of the downstream side air-fuel ratio sensor is a predetermined value other than zero, it is judged that the air-fuel ratio of the exhaust gas flowing out from the upstream side exhaust purification catalyst 20 has become the rich judged air-fuel ratio.

Note that, in this Description, the oxygen storage amount of the exhaust purification catalyst is explained as changing between the maximum oxygen storage amount and zero. This means that the amount of oxygen, which can be further stored by the exhaust purification catalyst, changes between zero (when oxygen storage amount is maximum oxygen storage amount) and the maximum value (when oxygen storage amount is zero).

5. combustion chamber
6. intake valve
8. exhaust valve
10. spark plug
11. fuel injector
13. intake branch pipe
15. intake pipe
18. throttle valve
19. exhaust manifold
20. upstream side exhaust purification catalyst
21. upstream side casing
22. exhaust pipe
23. downstream side casing
24. downstream side exhaust purification catalyst
31. ECU
39. air flow meter
40. upstream side air-fuel ratio sensor
41. downstream side air-fuel ratio sensor

The invention claimed is:

1. A control system of an internal combustion engine, the engine comprising an exhaust purification catalyst, which is arranged in an exhaust passage of the internal combustion engine and which can store oxygen, the control system comprising:
a downstream side air-fuel ratio sensor, which is arranged at a downstream side, in a direction of flow of exhaust, of the exhaust purification catalyst and which detects an air-fuel ratio of an outflow exhaust gas flowing out from the exhaust purification catalyst; and
an electronic control unit (ECU) including a CPU, memory, an input port, and an output port, the ECU programmed to:
control an air-fuel ratio of an inflow exhaust gas flowing into the exhaust purification catalyst;
increase an oxygen storage amount of the exhaust purification catalyst by continuously or intermittently setting a target air-fuel ratio of the inflow exhaust gas to leaner than a stoichiometric air-fuel ratio, when the air-fuel ratio of the outflow exhaust gas detected by the downstream side air-fuel ratio sensor becomes richer than the stoichiometric air-fuel ratio and until the oxygen storage amount becomes a predetermined storage amount, the predetermined storage amount being smaller than an upper limit oxygen storage amount, the upper limit oxygen storage amount being a point where rates of rise of concentrations of oxygen and $NO_X$ in the outflow exhaust gas start to increase; and
decrease the oxygen storage amount by continuously or intermittently setting the target air-fuel ratio to richer than the stoichiometric air-fuel ratio, when the oxygen storage amount becomes the predetermined storage amount or more, so that the oxygen storage amount decreases toward zero without reaching a maximum oxygen storage amount.

2. The control system of an internal combustion engine according to claim 1, wherein a difference between an average value of said target air-fuel ratio and the stoichiometric air-fuel ratio in the time period when the target air-fuel ratio is continuously or intermittently set to leaner than the stoichiometric air- fuel ratio in order to increase the oxygen storage amount is larger than a difference between an average value of said target air-fuel ratio and the stoichiometric air-fuel ratio in the time period when the target air-fuel ratio is continuously or intermittently set to richer than the stoichiometric air-fuel ratio in order to decrease the oxygen storage amount.

3. The control system of an internal combustion engine according to claim 1, wherein said ECU is programmed to continuously maintain said target air-fuel ratio leaner than the stoichiometric air-fuel ratio in order to increase the oxygen storage amount.

4. The control system of an internal combustion engine according to claim 1, wherein said ECU is programmed to continuously maintain said target air-fuel ratio richer than the stoichiometric air-fuel ratio in order to decrease the oxygen storage amount.

5. The control system of an internal combustion engine according to claim 1, wherein said ECU is programmed to, when decreasing the oxygen storage amount, intermittently set said target air-fuel ratio to richer than the stoichiometric air-fuel ratio, and set said target air-fuel ratio to leaner than the stoichiometric air-fuel ratio in at least a part of a time period when said target air-fuel ratio is not set to the stoichiometric air-fuel ratio.

6. The control system of an internal combustion engine according to claim 1, further comprising an upstream side air-fuel ratio sensor, which detects the air-fuel ratio of the inflow exhaust gas,
wherein said ECU is programmed to control an amount of fuel supplied into a combustion chamber of said internal combustion engine so that the air-fuel ratio of the inflow exhaust gas that is detected by said upstream side air-fuel ratio sensor, becomes said target air-fuel ratio.

7. The control system of an internal combustion engine according to claim 6, wherein the ECU is programmed to estimate the oxygen storage amount based on the air-fuel ratio of the inflow exhaust gas detected by said upstream side air-fuel ratio sensor,
wherein said ECU is programmed to set said target air-fuel ratio to leaner than the stoichiometric air-fuel ratio until the oxygen storage amount estimated by said ECU becomes said predetermined storage amount, when increasing the oxygen storage amount.

8. The control system of an internal combustion engine according to claim 1, wherein the internal combustion engine further comprises a downstream side exhaust purification catalyst which is arranged in the exhaust passage at the downstream side, in the direction of flow of exhaust, of said downstream side air-fuel ratio sensor and which can store oxygen.

9. The control system of an internal combustion engine according to claim 1, wherein the ECU is programmed to alternatingly and repeatedly increase and decrease the oxygen storage amount.

10. A control system of internal combustion engine, the engine comprising an exhaust purification catalyst, which is arranged in an exhaust passage of the internal combustion engine and which can store oxygen, the control system comprising:
a downstream side air-fuel ratio sensor, which is arranged at a downstream side, in a direction of flow of exhaust, of the exhaust purification catalyst and which detects an air-fuel ratio of an outflow exhaust gas flowing out from the exhaust purification catalyst;
an upstream side air-fuel ratio sensor, which detects an air-fuel ratio of an inflow exhaust gas flowing into the exhaust purification catalyst; and
an electronic control unit (ECU) including a CPU, memory, an input port, and an output port, the ECU programmed to:
control the air-fuel ratio of the inflow exhaust gas;
estimate an oxygen storage amount of said exhaust purification catalyst based on the air-fuel ratio of the inflow exhaust gas which is detected by said upstream side air-fuel ratio sensor;
increase the oxygen storage amount by continuously or intermittently setting a target air-fuel ratio of the inflow exhaust gas to leaner than a stoichiometric air-fuel ratio, when the air-fuel ratio of the outflow exhaust gas detected by said downstream side air-fuel ratio sensor becomes richer than the stoichiometric air-fuel ratio and until the oxygen storage amount becomes a predetermined storage amount, the predetermined storage amount being smaller than an upper limit oxygen storage amount, the upper limit oxygen storage amount being a point where rates of rise of concentrations of oxygen and $NO_X$ in the outflow exhaust gas start to increase; and
decrease the oxygen storage amount by continuously or intermittently setting said target air-fuel ratio to richer than the stoichiometric air-fuel ratio, when the oxygen storage amount becomes said predetermined storage amount or more, so that said oxygen storage amount decreases toward zero without reaching a maximum oxygen storage amount.

11. The control system of an internal combustion engine according to claim 10, wherein a difference between an average value of said target air-fuel ratio and the stoichiometric air-fuel ratio in the time period when the target air-fuel ratio is continuously or intermittently set to leaner than the stoichiometric air-fuel ratio in order to increase the oxygen storage amount is larger than a difference between an average value of said target air-fuel ratio and the stoichiometric air-fuel ratio in the time period when the target air-fuel ratio is continuously or intermittently set to richer than the stoichiometric air-fuel ratio in order to decrease the oxygen storage amount.

12. The control system of an internal combustion engine according to claim 10, wherein said ECU is programmed to continuously maintain said target air-fuel ratio leaner than the stoichiometric air-fuel ratio in order to increase the oxygen storage amount.

13. The control system of an internal combustion engine according to claim 10, wherein said ECU is programmed to continuously maintain said target air-fuel ratio richer than the stoichiometric air-fuel ratio in order to decrease the oxygen storage amount.

14. The control system of an internal combustion engine according to claim 10, wherein said ECU is programmed to, when decreasing the oxygen storage amount, intermittently set said target air-fuel ratio to richer than the stoichiometric air-fuel ratio, and set said target air-fuel ratio to leaner than the stoichiometric air-fuel ratio in at least a part of a time period when said target air-fuel ratio is not set to the stoichiometric air-fuel ratio.

15. The control system of an internal combustion engine according to claim 10, wherein said ECU is programmed to control an amount of fuel supplied into a combustion chamber of said internal combustion engine so that the air-fuel ratio of the inflow exhaust gas that is detected by said upstream side air-fuel ratio sensor, becomes said target air-fuel ratio.

16. The control system of an internal combustion engine according to claim 15, wherein said ECU is programmed to set said target air-fuel ratio to leaner than the stoichiometric air-fuel ratio until the oxygen storage amount estimated by said ECU becomes said predetermined storage amount.

17. The control system of an internal combustion engine according to claim 10, wherein the internal combustion engine further comprises a downstream side exhaust purification catalyst, which is arranged in the exhaust passage at the downstream side, in the direction of flow of exhaust, of said downstream side air-fuel ratio sensor and which can store oxygen.

18. The control system of an internal combustion engine according to claim 10, wherein the ECU is programmed to alternatingly and repeatedly increase and decrease the oxygen storage amount.

* * * * *